United States Patent
Ouni et al.

(10) Patent No.: US 12,318,501 B2
(45) Date of Patent: Jun. 3, 2025

(54) DISINFECTION CHAMBERS AND TUNNELS

(71) Applicant: Innovative Health Solutions, Inc., Walnut Creek, CA (US)

(72) Inventors: Raouf Ouni, Drancy (FR); Farid Fattoum, Concord, CA (US)

(73) Assignee: Innovative Health Solutions, Inc., Walnut Creek, CA (US)

( * ) Notice: Subject to any disclaimer, the term of this patent is extended or adjusted under 35 U.S.C. 154(b) by 707 days.

(21) Appl. No.: 17/764,159

(22) PCT Filed: Jun. 14, 2021

(86) PCT No.: PCT/US2021/037243
§ 371 (c)(1),
(2) Date: Mar. 25, 2022

(87) PCT Pub. No.: WO2021/257460
PCT Pub. Date: Dec. 23, 2021

(65) Prior Publication Data
US 2022/0370673 A1    Nov. 24, 2022

Related U.S. Application Data

(60) Provisional application No. 63/039,308, filed on Jun. 15, 2020.

(51) Int. Cl.
*A61L 2/26* (2006.01)
*A61B 5/01* (2006.01)
(Continued)

(52) U.S. Cl.
CPC .................. *A61L 2/26* (2013.01); *A61L 2/183* (2013.01); *A61L 2/24* (2013.01); *A61B 5/01* (2013.01);
(Continued)

(58) Field of Classification Search
None
See application file for complete search history.

(56) References Cited

U.S. PATENT DOCUMENTS 4,971,818 A    11/1990 Pye
5,520,893 A    5/1996 Kasting, Jr. et al.
(Continued)

FOREIGN PATENT DOCUMENTS

AU    2010200764    3/2010
KR    10-1263488    6/2013
WO    WO 2021/257460    12/2021

OTHER PUBLICATIONS

KR 101263488 B1 with machine translation (Year: 2013).*
(Continued)

*Primary Examiner* — Natasha E Young
(74) *Attorney, Agent, or Firm* — Makoui Law, PC; Ali Makoui

(57) ABSTRACT

A disinfection tunnel includes an enclosure, an ozonated water tank, an ozonated water generator, a set of nozzles, a mist generator, and a processor. The ozonated water generator generates ozonated water and stores the ozonated water in the tank. When a person enters the enclosure, the processor starts the mist generator. The mist generator receives ozonated water from the tank, turns the ozonated water to a mist of ozonated water, and pumps the mist of ozonated water to the nozzles. The nozzles spray the mist of ozonated water inside the enclosure for a time period.

21 Claims, 14 Drawing Sheets

(51) Int. Cl.
*A61L 2/18* (2006.01)
*A61L 2/24* (2006.01)

(52) U.S. Cl.
CPC ...... *A61L 2202/11* (2013.01); *A61L 2202/122* (2013.01); *A61L 2202/14* (2013.01); *A61L 2202/15* (2013.01)

(56) References Cited

U.S. PATENT DOCUMENTS

| | | | |
|---|---|---|---|
| 5,533,305 | A | 7/1996 | Bielecki |
| 5,957,044 | A | 9/1999 | Kravitz |
| 6,379,633 | B1 * | 4/2002 | Garlick .................. A23B 2/792 422/305 |
| 6,443,164 | B1 | 9/2002 | Parker et al. |
| 7,128,872 | B2 * | 10/2006 | Robitaille ............... A61L 2/202 204/194 |
| 7,275,982 | B1 * | 10/2007 | Brandt .................. A22B 5/0082 452/177 |
| 8,201,288 | B2 | 6/2012 | Thomason et al. |
| 10,017,409 | B2 | 7/2018 | Hengsperger et al. |
| 10,426,852 | B2 | 10/2019 | Dobrinsky et al. |
| 2003/0000539 | A1 | 1/2003 | Laughlin |
| 2004/0131519 | A1 | 7/2004 | Amedeo et al. |
| 2005/0193945 | A1 | 9/2005 | Coffield et al. |
| 2008/0292498 | A1 | 11/2008 | Resch et al. |
| 2010/0001097 | A1 | 1/2010 | Spivak |
| 2012/0015043 | A1 | 1/2012 | Heacox |
| 2015/0217010 | A1 | 8/2015 | Whitney |
| 2016/0008503 | A1 | 1/2016 | Webb et al. |
| 2017/0135528 | A1 | 5/2017 | Allred et al. |
| 2017/0224858 | A1 | 8/2017 | Stibich |
| 2018/0008734 | A1 | 1/2018 | Andersen et al. |
| 2018/0055957 | A1 | 3/2018 | Lu et al. |
| 2019/0099507 | A1 | 4/2019 | Garrett |
| 2019/0174780 | A1 | 6/2019 | Larson |
| 2019/0351080 | A1 | 11/2019 | Turbett |

OTHER PUBLICATIONS

International Search Report and Written Opinion of PCT/US2021/037243, Sep. 23, 2021 (mailing date), Innovative Health Solutions, Inc.

\* cited by examiner

DISINFECTION CHAMBERS AND TUNNELS

CLAIM OF BENEFIT TO PRIOR APPLICATIONS

This application is a national stage application of PCT Application PCT/US21/37243, filed on Jun. 14, 2021, now published as WO 2021/257460. PCT Application PCT/US21/37243_claims the benefit of U.S. Provisional Patent Application Ser. No. 63/039,308, filed on Jun. 15, 2020. The contents of PCT Application PCT/US21/37243, published as WO 2021/257460 and U.S. Provisional Patent Application 63/039,308 are hereby incorporated by reference.

BACKGROUND

World Health Organization (WHO) has retained the use of a six-phased approach for incorporation of new recommendations and approaches into the existing national preparedness and response plans. On Jun. 11, 2009, WHO declared that all criteria for a pandemic have been met and raised to phase 6 the transmission of New influenza A (H1N1). A declaration that provided fear across the world and eventually between 200,000 and 400,000 people died across many countries.

In 2012, another virus MERS-CoV occurred in Saudi Arabia and killed 2,500 people in 27 countries. Then the Ebola virus reappeared in 2014 in West Africa, causing 11,000 deaths between 2014 and 2016. A very heavy toll due in particular to the high mortality of the virus. Next, ZIKA virus occurred in 2016. In December 2019, the coronavirus disease 2019 (COVID-19) was first identified in China, and then resulted in a pandemic in the rest of the world. With the advent of COVID-19, the world has come to a total lockdown, effecting all sectors of the economy such as, airports, malls, stadiums, movie theaters, small and large business, etc.

It may be observed that the occurrence of new viruses has been periodical and that approximately every two to three years there has been a new threat to our species. It is, therefore, imperative to produce a solution that could stop the spread of the viruses and other harmful microorganisms pathogens.

BRIEF DESCRIPTION OF THE DRAWINGS

The various embodiments of the present disinfection chambers and tunnels now will be discussed in detail with an emphasis on highlighting the advantageous features. These embodiments depict the novel and non-obvious disinfection chambers and tunnels shown in the accompanying drawings, which are for illustrative purposes only. These drawings include the following figures, in which like numerals indicate like parts.

DETAILED DESCRIPTION

Figure 1:
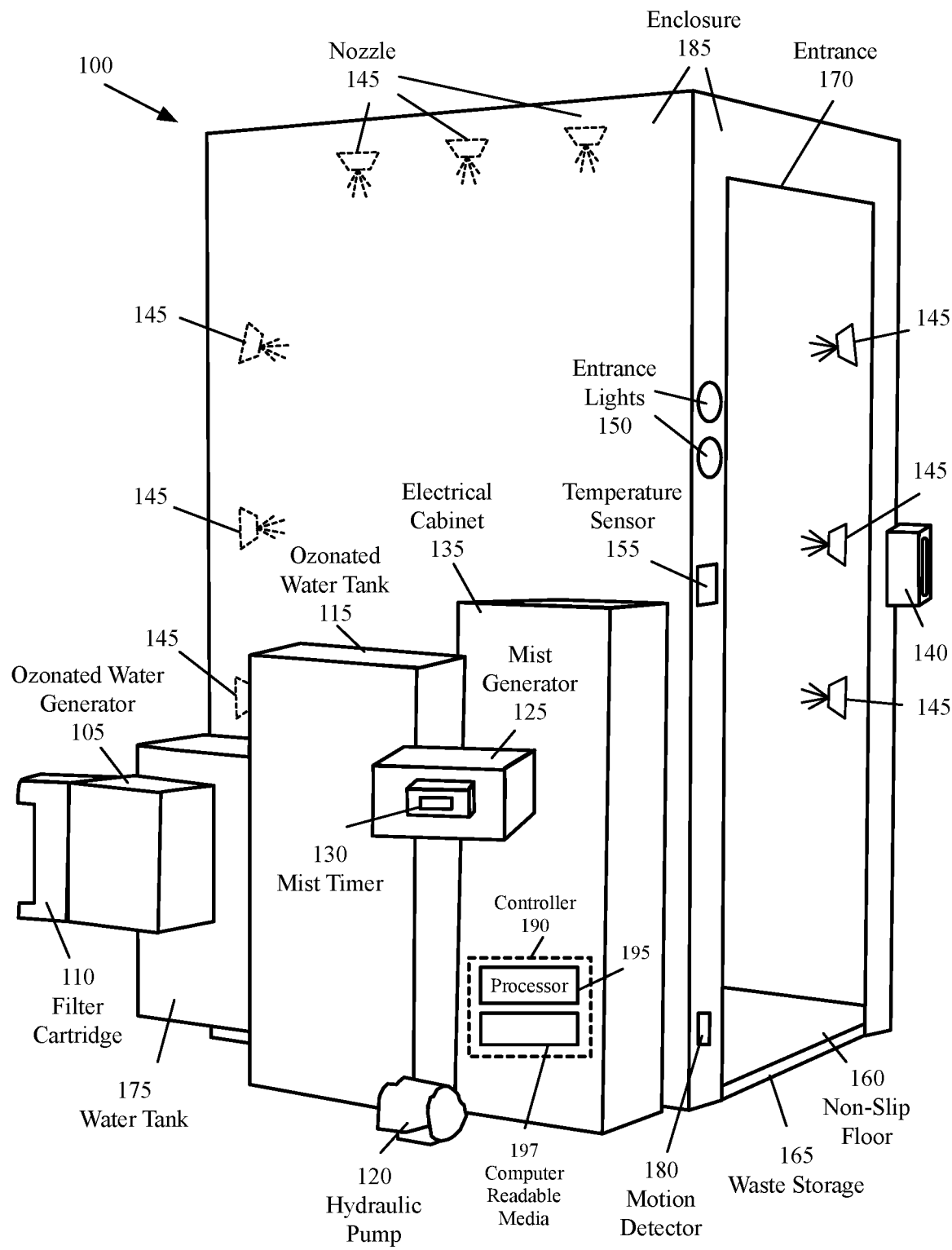
FIG. 1 is a front perspective of a disinfection tunnel, according to various aspects of the present disclosure.

One aspect of the present embodiments includes the realization that, the previous disinfectant tunnels used virucides that may have adverse effects on the health of people as well as the environment. Chemical virucides, ultraviolet (UV) lights, and/or ozone in gaseous form may be harmful to people and/or the environment.

The present embodiments, as described in detail below, solve the above-mentioned problem by using a natural and organic disinfectant that has no known harmful effects on human or environment. The embodiments of the present invention spray ozonated water on human, animals, and/or objects inside a tunnel. The ozonated water is generated from water molecules, a harmless mist is generated by a fog generator, and is sprayed inside the tunnel when the presence of humans, animals, and/or objects are detected inside the tunnel. Although ozone in the gaseous state may be harmful, in the liquid state it poses no danger to humans and environment.

The remaining detailed description describes the present embodiments with reference to the drawings. In the drawings, reference numbers label elements of the present embodiments. These reference numbers are reproduced below in connection with the discussion of the corresponding drawing features.

I. Disinfection Tunnel

FIG. 1 is a front perspective of a disinfection tunnel (or disinfection chamber) 100, according to various aspects of the present disclosure. The disinfection tunnel 100 may be used to disinfect people, animals, and/or objects. The disinfection tunnel 100 may be positioned, for example, and without limitations, at the entrance to offices and stores in order to disinfect people, animals, and objects (mobile electronic devices, trolleys, keys, bags, etc.).

With reference to FIG. 1, the disinfection tunnel 100 may include an ozonated water generator 105, an ozonated water generator filter cartridge 110, an ozonated water storage tank 115, a hydraulic pump 120, a mist (or fog) generator 125, a mist timer 130, a water storage tank 175, an electrical cabinet 135, a contactless gel dispenser 140, one or more mist nozzles 145, one or more entrance lights 150, a temperature sensor 155, a non-slip floor 160, a waste storage 165, an enclosure (or housing) 185, and/or a motion detector 180. The piping used for carrying the fluid between different components of the disinfection tunnel 100, such as, the water tank 175, the ozonated water generator 105, the ozonated water tank 115, the pump 120, the mist generator 125, the nozzles 145, etc., is not shown in FIG. 1 for simplicity.

The ozonated water generator 105 may be an on-board biocidal generator configured to generate stabilized aqueous ozone (or ozonated water). The ozonated water generator 105 may transform cold tap water into a pure active ingredient with multiple properties, referred to as "ozonated water." The stabilized ozonated water is a powerful natural deodorant and disinfectant cleaner. The disinfection tunnel 100 of the present embodiments may eliminate 99.99% of pathogens, such as bacteria, viruses, fungi spores, etc., in a single pass without any chemical additives. The disinfection tunnel 100 may be used, for example, and without limitations, for disinfecting people, animals, and objects against viruses, such as, COVID-19.

Water (e.g., cold tap water), in some embodiments, may be stored in the water tank 175. The water may be provided from the water tank 175, for example by a pump (not shown) to the ozonated water generator 105. In other embodiments, water may be provided to the ozonated water generator 105 by connecting the ozonated water generator 105 to a tap water pipe (e.g., cold water brought in by a pipe connected to a municipality's water pipes).

The ozonated water generator filter cartridge 110 may be used to filter water supplied to ozonated water generator 105. The tap water in different localities may include different types and different quantities of minerals and impurities. These minerals may affect the performance of aqueous ozone. The filter cartridge 110 stabilizes the tap water by adjusting the minerals and impurities in the water. Therefore, regardless of where in the world the disinfection tunnel 100 is used, the water entered in the ozonated water generator 105 is consistent and is configured for maximized cleaning and sanitizing performance.

The filter cartridge 110, may be periodically changed (e.g., and without limitations every 3,000 liters and/or after every 2 to 3 months of use). The ozonated water generated by the ozonated water generator 105 may be stored in the ozonated water tank 115.

The disinfection tunnel 100 may include a controller 190 inside the waterproof electrical cabinet 135. The controller 190 may include a processor 195 that may control the operations of the disinfection tunnel 100. The controller 190 may include computer readable media 197 (e.g., volatile memory and non-volatile memory) to store data and/or computer readable instructions.

Some embodiments may include the optional temperature sensor 155. In these embodiments, when a person approaches the disinfection tunnel 100, the temperature sensor 155, which may include an infrared sensor, may measure the person's body temperature and may send the measurement to the processor 195.

The processor 195 may receive the temperature measurement from the temperature sensor 155 and may compare the temperature measurement with a threshold temperature for a healthy person. When the temperature measurement exceeds the threshold, the processor may generate an alert signal (e.g., an audio signal and/or a visual signal) to alert the person not to enter the disinfection tunnel 100. In some embodiments, the disinfection tunnel 100 may include an entrance door (not shown) that may not open if the person has high temperature. For example, the processor 195 may control a door hinge or a door lock to prevent the tunnel's door to open when the temperature measurement exceeds the threshold.

Assuming that the person is allowed to enter the disinfection tunnel 100, the disinfection tunnel 100 may be used as follows. The person may optionally hold the hands in front of the contactless gel dispenser 140. The contactless gel dispenser 140 may include a sensor to detect the presence of the hands and may dispense a quantity of hand disinfectant, for example, and without limitations, hydroalcoholic gel to disinfect the person's hands.

When the person enters the disinfection tunnel 100 through the entrance 170, the motion detector 180 (e.g., a photoelectric detector) may detect that the person has entered the disinfection tunnel 100 and may send one or more signals to the processor 195. In response to receiving the signal(s) from the motion detector, the processor 195 may trigger a misting operation by the mist generator 125. It should be noted that some embodiments may trigger the misting operation in response to signal(s) other than the signal(s) received from a motion detector. For example, the misting operation may be started in response to receiving one or more signals from a button inside the enclosure that may be activated (e.g., pressed) by a person inside the enclosure, in response to receiving one or more signals from a button outside the enclosure that may be activated (e.g., pressed) by a person/operator outside the enclosure after a person enters the enclosure, in response to receiving one or more signals from a sensor indicating that an entrance door of the disinfection tunnel is closed, in response to receiving one or more signals from a sensor installed on the floor of the enclosure indicating that a weight exceeding a threshold is detected, etc.

The controller, in some embodiments, may start a timer for the duration of the misting operation. The value of the timer, in some embodiments, may be programmed in the controller 190. In other embodiments, the value of the timer may be manually set by the mist timer 130 (e.g., the value of the timer may be set by an operator after the tunnel is set up and the power is applied to the electrical components of the tunnel). For example, and without limitations, the value of the mist timer may be set to 30 seconds in some embodiments.

It should be noted that although the timer 130 is shown as a separate physical timer, the timer may be implemented as an internal timer of the controller 190 in some embodiments. In these embodiments, the internal timer may be a software and/or hardware implemented timer. The value of the internal timer may be programmed into the software executed by the processor 195, may be received from an external electronic device that is authorized to communicate with the processor 195, may be received through a user interface of a display terminal (not shown) that is communicatively coupled to the processor 195, etc.

The mist generating nozzles 145 may be configured such that the person's body and clothing may not get wet. For example, in some embodiments, the nozzles 145 may be configured to operate at a high pressure (e.g., and without limitations at a pressure of between 55 bars and 65 bars, at a pressure of more than 55 bars, at a pressure of substantially 60 bars, depending on the configuration). The ozonated water droplets in the mist at the configured pressure evaporate fairly quickly and, therefore, the person's body and clothing may not get wet.

With further reference to FIG. 1, when the person enters the disinfection tunnel 100, an entrance light 150 may turn red to indicate that the disinfection is in progress. After the misting duration is over, the person is completely disinfected and may exist through an exit (not shown) in the back of the enclosure 185. The red entrance light may then be turned off and a green entrance light 150 may be turned on. Some embodiments may include two separate entrance lights, a green light and a red light, as described above. Other embodiments may include one entrance light that may switch between green and red. The entrance light(s) 150 may operate as a traffic light to warn in the event of a queue and to prevent two people from finding themselves in the tunnel at the same time. In addition to, or in lieu of, the lights 150, some embodiments may use a display to show a message or a sign indicating whether the tunnel 100 is occupied.

The enclosure 185, in some embodiments, may be configured for use by a few persons at a time. For example, an individual person, a limited number of persons (e.g., a person with one or more children), etc. Examples of large flow disinfection tunnels for simultaneous use by many persons are provided in Section II, below. The enclosure 185, in some embodiments, may include a door or a plastic cover with and opening to allow a person to enter the tunnel 100. The door, in some embodiments, may be locked and unlocked (e.g., by receiving one or more signals from the processor 195). In some embodiments, the entrance to the enclosure 185 may always be open (e.g., with no door or covering). The enclosure 185, in some embodiments, may include an exit door or a plastic cover with and opening to allow a person to exit the tunnel 100. In some embodiments, the exit to the enclosure 185 may always be open (e.g., with no door or covering).

The disinfection tunnel 100 may include a non-slip floor 160 that may include a carpet or fabric that may absorb the mist and may disinfect the footwear of the person. Any excess water or ozonated water may be collected in the waste storage 165 that may either have a pipe (not shown) to empty the excess water (e.g., to a sewage line) or may be manually emptied. For example, the disinfection tunnel 100 may include a sensor 355 (FIG. 3) that may sense the level of liquid in the waste storage 165 and may generate one or more signals when the waste liquid in the waste storage 165 exceeds a threshold. The processor 195 may receive the signal(s) from the sensor and may generate one or more signals, for example, to an attendant, to empty and/or replace the wastewater storage 165.

The ozonated water generator 105 generates stabilized aqueous ozone. The ozonated water generator 105 may receive water either from the water tank 175 or from a tap water pipe and may transform the water into stabilized aqueous ozone (SAO), which is a powerful natural disinfectant. The disinfecting capacity of ozone O3 is used by transforming oxygen (O2) into ozone O3 or Trioxygen, which is mixed with water. The bonds between the three oxygen atoms are simple bonds and easily decomposes into three free atoms and forms the oxygen O2.

The ozonated water is then poured into the ozonated water tank 115 (e.g., and without limitations at a rate of between 5 to 20 liters per minutes). The pump 120 (e.g., a dosing hydraulic pump) may receive one or more signals from the processor 195 and may inject the SAO, from the ozonated water tank 115, into the mist generator 125. The mist generator 125 may generate the disinfectant mist through the nozzles 145. The dosing hydraulic pump 120 may be controlled by the processor 195 of the controller 195 to provide the ozonated water to the mist generator 125 at a predetermined rate. The mist generator 125, in some embodiments, may use ultrasound, piezoelectric effect, etc., to generate vibrations in the ozonated water in order to convert the ozonated water into ozonated water mist. The mist generator 125, in some embodiments, may include an internal pump, and/or may act as a high pressure pump, that transfers the mist of ozonated water under pressure, through one or more pipes, to the nozzles 145. The nozzles 145 may be configured to spray the mist under pressure. For example, and without limitations, the nozzles 145, in different embodiments, may be configured to operate at a pressure of between 55 bars and 65 bars, at a pressure of more than 55 bars, at a pressure of substantially 60 bars, etc. The mist may last for a predetermine amount of time (e.g., and without limitations, 30 seconds).

With reference to FIG. 1, the disinfection tunnel 100 is an effective and natural disinfection device. The disinfection tunnel 100 uses ozonized water without any chemical additive. The disinfection tunnel 100 is adaptable to different configurations (such as, e.g., and without limitations, movie theaters, stadiums, factories, offices, residential buildings, shopping centers, etc.). The disinfection tunnel 100, therefore, helps the resumption of activities by creating a healthy and safe environment for all individuals.

Figure 2:
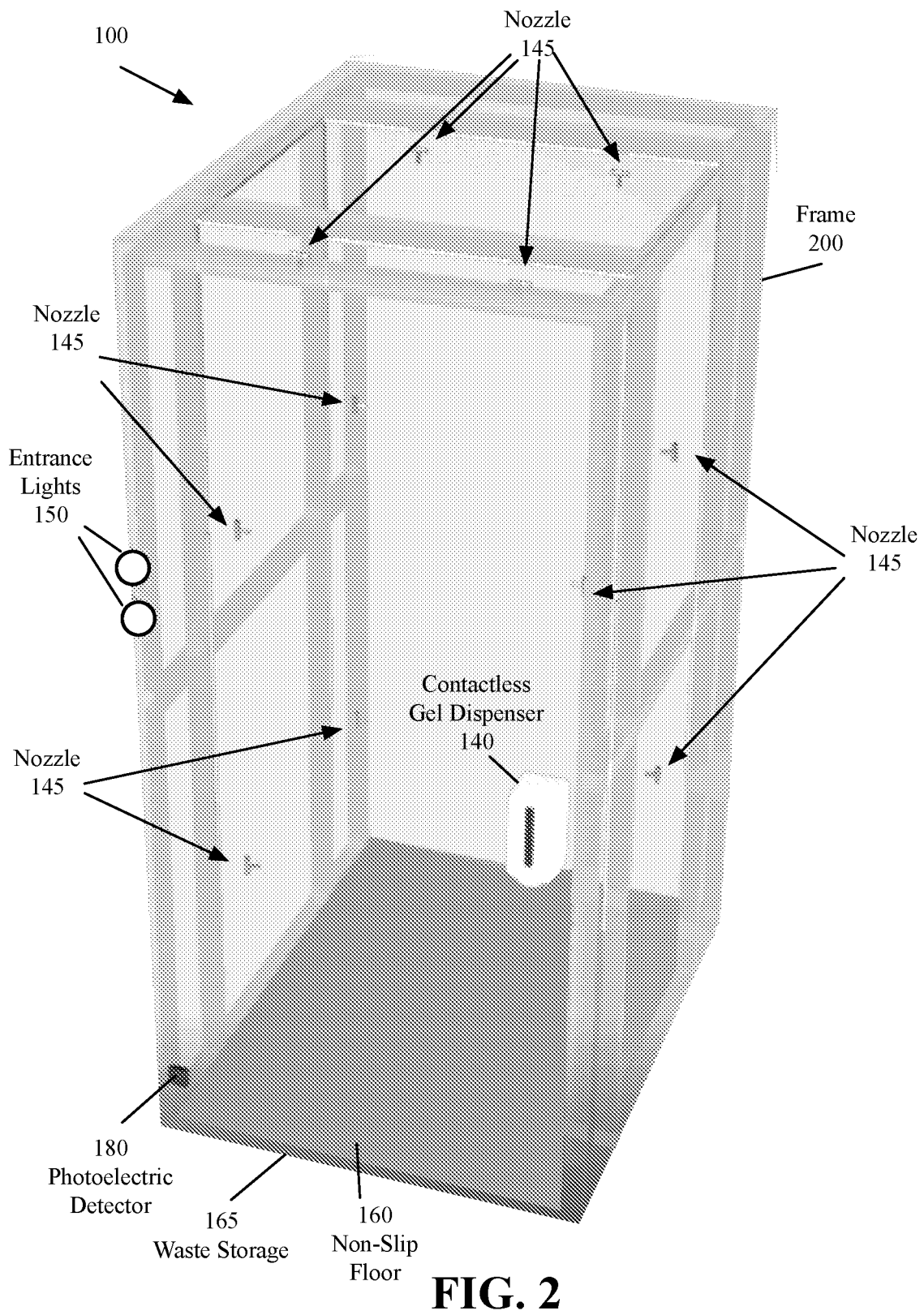
FIG. 2 is a front perspective of the structural frame of the disinfection tunnel of FIG. 1, according to various aspects of the present disclosure.

FIG. 2 is a front perspective of the structural frame 200 of the disinfection tunnel 100 of FIG. 1, according to various aspects of the present disclosure. With reference to FIG. 2, an exemplary position of the misting nozzles 145 are shown. The piping used for carrying the fluid between different components of FIG. 2 is not shown for simplicity. The structural frame 200 and the electrical wirings (not shown) are configured in accordance with safety standards to prevent electrical shock. The disinfection tunnel 100 may be equipped with a lightning rod (not shown) and electrically grounded. In some embodiments, all equipment may be provided with a minimum IP55 waterproof rating.

The ozone is very effective at killing bacteria, viruses, and fungi spores, and removes oxidizing odors, stains, and/or dirt. Ozone stabilized up to 24 hours, is chemical free, and is 50% stronger than bleach. The disinfection tunnel 100 generates ozone artificially by utilizing an electrical charge and then infusing the ozone into water creating the aqueous ozone. The disinfection tunnel 100 transforms the ordinary tap water into aqueous ozone on site with a continuous flow rate to fill the ozonated water tank 115, which may supply the nozzles 145. The aqueous ozone stored in the ozonated water tank 115 preserves its cleaning properties for days and safely reverts back to water and O2 after use.

With reference to FIG. 1, some embodiments may use an off-the-shelf ozonated water generator 105. Cold water may enter the filter cartridge 110. The filtered water may then enter the ozonated water generator 105. The oxygen is also entered in the ozonated water generator 105 (e.g., and without limitations, oxygen in the atmospheric air may be drawn from the surrounding air through an air intake). A high voltage (e.g., and without limitations, 4,500 volts) may be used by the ozonated water generator 105 to transform the oxygen O2 to ozone O3. For example, in some embodiments, ozone may be generated by an electrical discharge (e.g., by a spark generated within the ozonated water generator 105) that splits an oxygen molecule (O2) into two unstable oxygen atoms. The oxygen atoms may combine with other oxygen molecules (O2) to form ozone (O3). The ozone is then infused into the water. The ozone may be infused into the water within the ozonated water generator 105 by a pump (not shown), by venturi effect (the reduction in the water pressure that results when the fluid flows through a constricted section of pipe), etc. Although Ozone is an unstable gas in its free form, when dissolves in the water, provides stabilized ozonated water. Any ozone gas that is not saturated in the water may be separated and safely dispensed.

Figure 3:
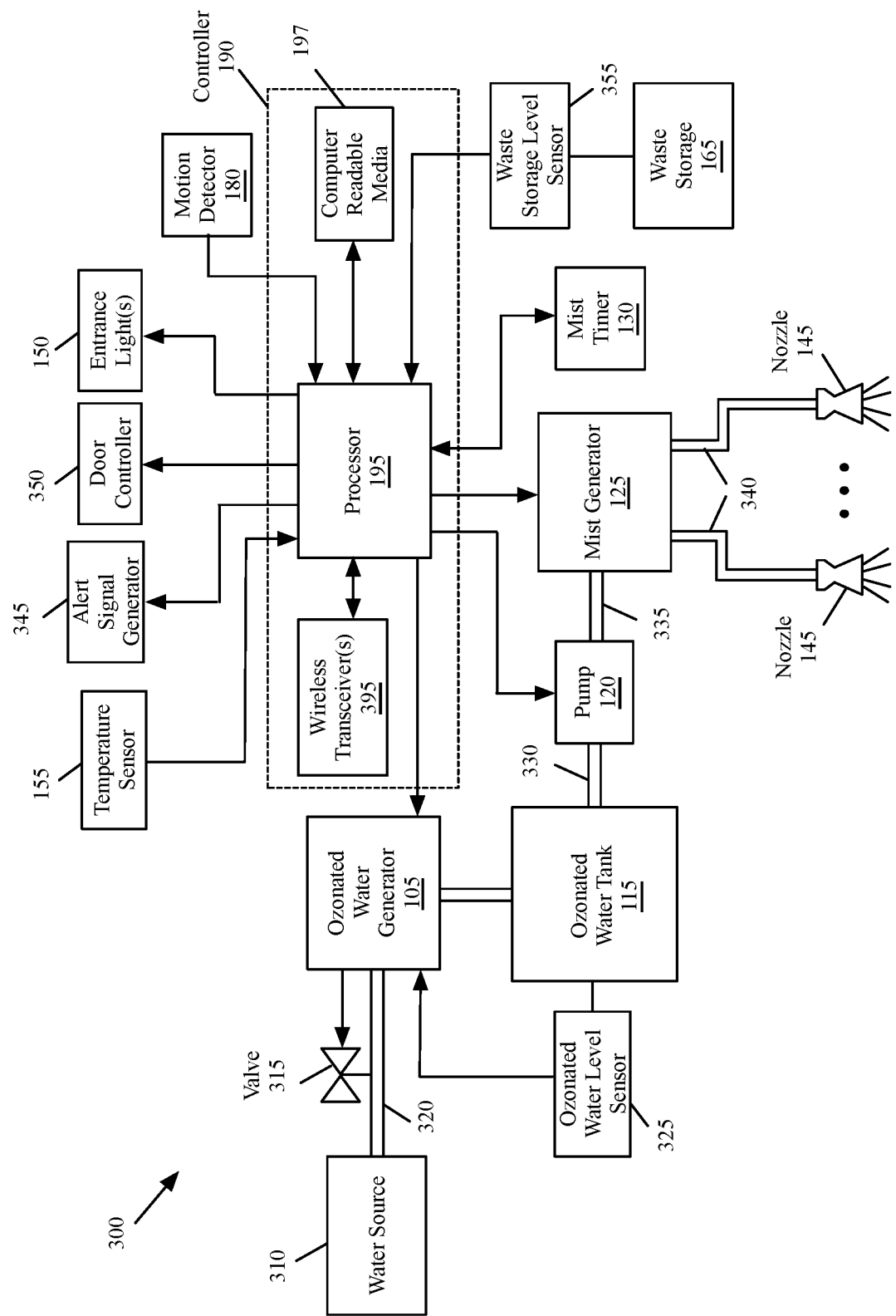
FIG. 3 is a functional block diagram illustrating an example mechanical and electrical system for the disinfection tunnel of FIGS. 1 and 2, according to various aspects of the present disclosure.

FIG. 3 is a functional block diagram illustrating an example mechanical and electrical system for the disinfection tunnel of FIGS. 1 and 2, according to various aspects of the present disclosure. With reference to FIG. 3, the system 300 may include a controller 190, a processor 195, computer readable media 197, one or more wireless transceivers 395, an ozonated water generator 105, an ozonated water tank 115, a pump 120, a mist generator 125, a mist timer 130, one or more entrance lights 150, a temperature sensor 155, a motion detector 180, a water source 310, an ozonated water level sensor 325, an alert signal generator 345, a door controller 350, one or more wireless transceivers 395, a waste storage 165, and/or a waste storage level sensor 355.

It should be noted that some of the components of FIG. 3, such as, the mist timer 130, the entrance light(s) 150, the temperature sensor 155, the ozonated water level sensor 325, the alert signal generator 345, the door controller 350, the wireless transceiver(s) 395, the waste storage 165, and/or the waste storage level sensor 355 may be optional and some of the present embodiments may not include one or more of these components.

With further reference to FIG. 3, the controller 190 may include the processor 195, the computer readable media 197, and the wireless transceiver(s) 395. The computer readable media 197 may be non-transitory computer readable media. The computer readable media 197 may include different types of memory units, such as, read-only-memory, volatile read-and-write memory, and/or non-volatile read-and-write memory. The read-only-memory may store static data and instructions that are needed by the processor 195. The non-volatile read-and-write memory may store instructions and data even when the power to the non-volatile memory is off. Some embodiments may use a mass-storage device (such as a magnetic or optical disk and its corresponding disk drive) as the non-volatile read-and-write memory.

The volatile read-and-write memory device may be random access memory and may be used as system memory. The system memory may store some of the instructions and data that the processor needs at runtime. In some embodiments, the processes of the present embodiments may be stored in the system memory, the non-volatile memory, and/or the read-only memory. From these various memory units, the processor 195 may retrieve instructions to execute and data to process in order to execute the processes of some embodiments. The wireless transceiver(s) 395 may be, for example, and without limitations, cellular transceiver(s), Wireless Local Area Network (WLAN) transceiver(s), Worldwide Interoperability for Microwave Access (WiMax) transceiver(s), HD Radio™ transceiver(s), Ultra-wideband (UWB) transceiver(s), ZigBee transceiver(s), Radio-Frequency Identification (RFID) transceiver(s), and/or 60 GHz transceiver(s).

With reference to FIG. 3, the processor 195 may receive a body temperature measurement from the temperature sensor 155 when a person approaches the disinfection tunnel 100 (FIG. 1). When the temperature measurement is more than a threshold temperature that may indicate the person has a fever, the processor 195 may generate an alert signal through the alert signal generator 345. The alert signal generator 345 may be a light signal that may turn on (e.g., a red light), a display screen (that may receive an alert message from the processor 195 and may display the message), a sound generator (that may sound an audible signal) to alert that the person has a high temperature and may not enter the disinfection tunnel.

The processor 195 may send a signal to the door controller 350 to keep the entrance door of the tunnel closed. For example, the door controller 350 may be an electronically controlled lock or an electronically controlled hinge that may receive one or more signals from the processor 195 and may prevent the entrance door to be opened.

When the person's body temperature is below the threshold, or when the system 300 does not include a temperature sensor, the processor 195 may receive one or more signals from the motion detector 180 indicating that a person has entered the disinfection tunnel. In response, the processor 195 may send one or more signals to the entrance light(s) 150 to set the light(s) to indicate that the tunnel is occupied. For example, when there is only one entrance light, the processor 195 may turn the entrance light red. When there are two entrance lights, the processor 195 may turn one of the lights to red and may turn off the other light. In addition to, or in lieu of the light signal, the processor 195 may display a message on a display screen (not shown) and/or play an audible message indicating that the disinfection tunnel is occupied.

The processor 195 may send one or more signals to the mist generator 125 to start the mist generator 125. The processor 195 may send one or more signals to the pump 120 to inject ozonated water (SAO) into the mist generator 125, through the pipes 330 and 335, at a predetermined rate. The processor 195 may start the mist timer 130. The mist timer 130 may be set by the processor 195, or by a person, to a time duration that mist is to be generated. The mist generator 125 may then generate the disinfectant mist of ozonated water (SAO) through the nozzles 145, which may be connected to the mist generator 125 through the pipes 340.

The processor 195 may receive one or more signals from the mist timer 130 when the timer expires. In response, the processor 195 may send one or more signals to the mist generator 125 and one or more signals to the pump 120 to stop. The ozonated water generator 105, in some embodiments, may be started or stopped by the processor 195. In other embodiments, the ozonated water generator 105 may include a separate controller (not shown), which may control the generation of the ozonated water based on the level of the ozonated water in the ozonated water tank 115.

The ozonated water generator 105 may generate ozone artificially by utilizing an electrical charge. The ozonated water generator 105 may receive water from the water source 310 and may infuse the ozone into water to generate the stabilized aqueous ozone. The water source 310 may be a water tank (such as the water tank 175 of FIG. 1) or may be the tap water (e.g., cold water brought in by a pipe connected to a municipality's water pipes). The water may be filtered to remove impurities before entering the ozonated water generator 105.

The ozonated water level sensor 325 may measure the level of ozonated water in the ozonated water tank 115 and may send the measurements to the controller of the ozonated water generator 105 or the processor 195. The operation of the ozonated water generator 105 may be controlled by the controller of the ozonated water generator 105 or the processor 195.

When the ozonated water level in the ozonated water tank 115 is below a first threshold, the ozonated water generator 105 may pour ozonated water into the ozonated water tank 115 until the ozonated water level in the ozonated water tank 115 is above a second threshold, which is higher than the first threshold. The controller of the ozonated water generator 105, or the processor 195, may close the valve 315 whenever the ozonated water generator 105 is not generating ozonated water to stop the flow of water into the ozonated water generator 105 through the pipe(s) 320.

It should be noted that some of the present embodiments may use a tankless ozonated water generated system. In these embodiments, instead of the ozonated water tank 115 of FIGS. 3, 7, and 13, the ozonated water generator 105 may be activated by the processor 195 whenever ozonated water is needed for the mist generator 125 to generate ozonated water and provide the ozonated water to the mist generator 125 through one or more pipes. For example, the processor 195 may start the ozonated water generator 105 a time period before the mist generator 125 is activated, the processor 195 may start the ozonated water generator 105 substantially at the same time as the mist generator 125 is started, etc. The processor 195 may stop the ozonated water generator 105 when the mist generator 125 is stopped and is not generating the ozonated water mist.

When the person leaves the tunnel, the processor 195 may receive one or more signals from a sensor (e.g., a motion detector) indicating that the person has left the disinfection tunnel. In response, the processor 195 may send one or more signals to the entrance light(s) 150 to set the light(s) to indicate that the tunnel is not occupied. For example, when there is only one entrance light, the processor 195 may turn the entrance light green. When there are two entrance lights, the processor 195 may turn one of the lights to green and may turn off the other light.

The waste storage 165 may be configured to collect ozonated water from the floor of the disinfection tunnel. The waste storage level sensor 355 may be configured to measure the level of ozonated water in the waste storage 165 and may send the measurements to the processor 195. The processor 195 may compare the level of the liquid in the waste storage 165. When the level of the liquid in the waste storage 165 exceeds a threshold, the processor 195 may generate one or more signals, through the wireless transceiver(s) 395, to one or more electronic devices external to the disinfection tunnel indicating that the waste storage 165 has to be emptied. The external electronic devices may be, for example, and without limitations, servers, mobile devices, etc., that may alert personnel to empty the waste storage 165. Alternatively, the processor 195 may turn on a light (not shown) or display a message to indicate that the waste storage 165 has to be emptied.

Figure 4A:
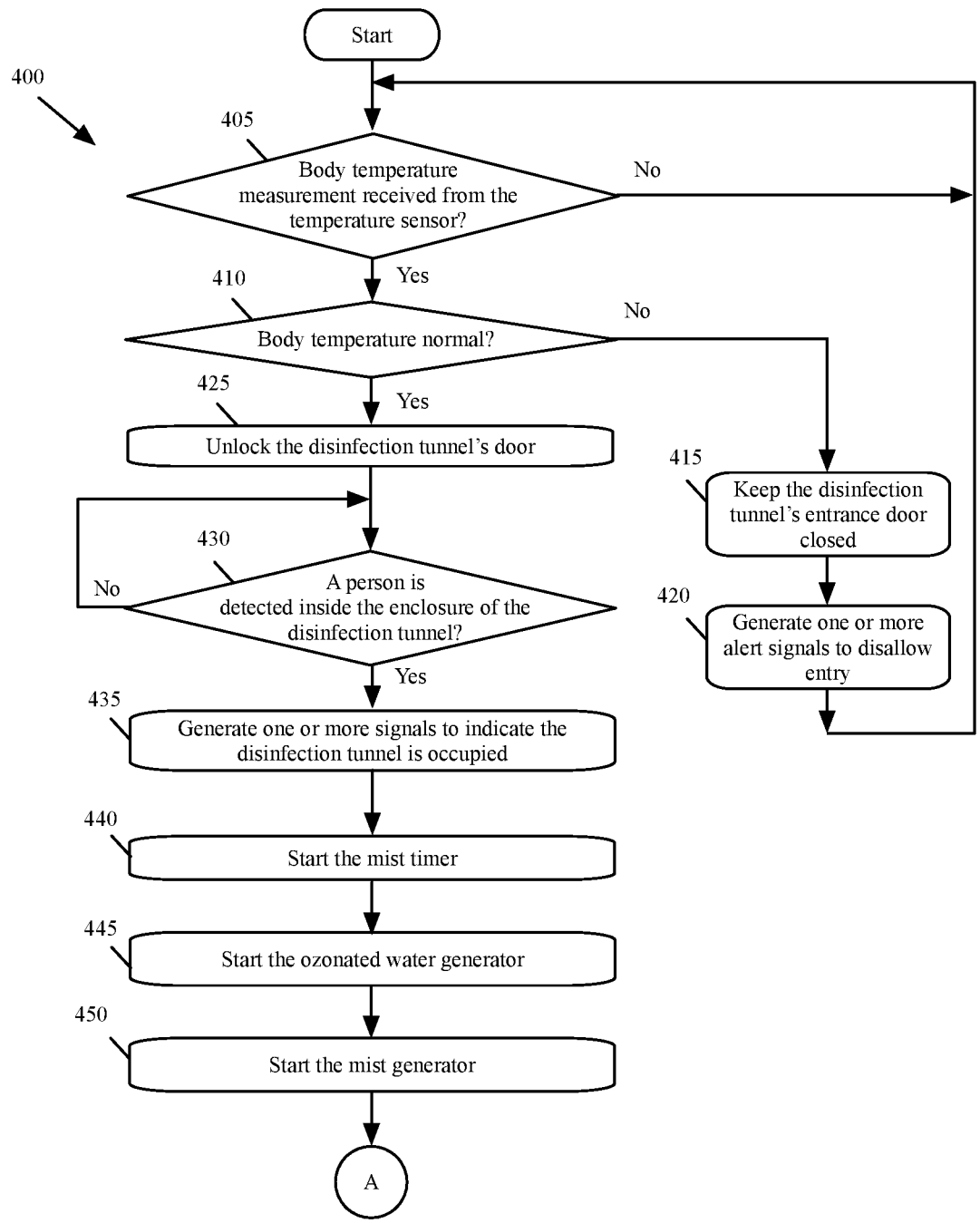
FIGS. 4A-4B illustrate a flowchart illustrating an example process for controlling a disinfection tunnel, according to various aspects of the present disclosure.
Figure 4B:
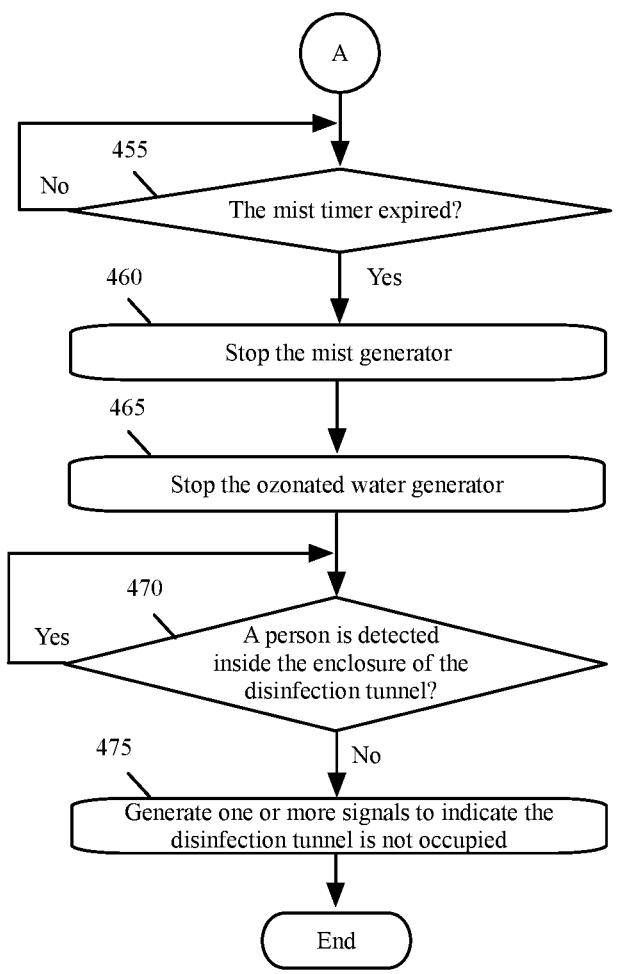

FIGS. 4A-4B illustrate a flowchart illustrating an example process 400 for controlling a disinfection tunnel, according to various aspects of the present disclosure. The process 400, in some embodiments, may be performed by the processor 195 (FIGS. 1 and 3) of a disinfection tunnel.

With reference to FIGS. 4A-4B, a determination may be made (at block 405) whether a body temperature measurement is received from the temperature sensor. For example, the processor 195 of FIGS. 1 and 3 may determine whether the temperature sensor 155 has read a person's body temperature. When body temperature reading is not received, the process 400 may return to block 405, which was described above.

Otherwise, a determination may be made (at block 410) whether the body temperature is normal. For example, the processor 195 of FIGS. 1 and 3 may determine whether the body temperature measurement is below a threshold, indicating that the person does not have a fever. If the body temperature is normal, the process 400 may proceed to block 425, which is described below. Otherwise, the tunnel's entrance door may be kept (at block 415) closed. For example, the processor 195 may keep the entrance door to the disinfection tunnel closed, as described above with reference to FIG. 3. One or more alert signals may be generated (at block 420) to disallow entry. For example, the processor 195 may turn on a light, display a message, and/or play an audio message indicating that the person should not enter the disinfection tunnel, as described above with reference to FIG. 3. The process 400 may then return to block 405, which was described above.

When it is determined (at block 410) that the body temperature is normal, the tunnel's entrance door may be unlocked (at block 425). For example, the processor 195 may open a luck or unlock a hinge to the entrance door of the disinfection tunnel, as described above with reference to FIG. 3.

A determination may be made (at block 430) whether a person is detected inside the enclosure of the disinfection tunnel. For example, the processor 195 (FIGS. 1 and 3) may receive one or more signals from the motion detector 180 indicating that is person has entered the disinfection tunnel. When a determination is made (at block 430) that the motion detector has not detected a person inside the disinfection tunnel, the process 400 may proceed to block 430, which was described above.

Otherwise, one or more signals may be generated (at block 435) to indicate the disinfection tunnel is occupied. For example, the processor 195 may turn on a light, display a message, and/or play an audio message indicating that the disinfection tunnel is occupied.

The mist timer may then be started (at block 440). For example, the processor 195 may start the mist timer 130 as described above, with reference to FIGS. 1 and 3. At block 445, the ozonated water generator may be started. For example, the processor 195 may start the ozonated water generator 105 as described above, with reference to FIGS. 1 and 3. At block 450, the mist generator may be started. For example, the processor 195 may start the mist generator 125 as described above, with reference to FIGS. 1 and 3.

A determination may be made (at block 455) whether the mist timer has expired. If not, the process 400 may proceed back to block 455, which was described above. Otherwise, the mist generator may be stopped (at block 460). For example, the processor 195 may generate one or more signals to stop the mist generator 125, as described above with reference to FIGS. 1 and 3. At block 465, the ozonated water generator may be stopped. For example, the processor 195 may generate one or more signals to stop the ozonated water generator 105, as described above with reference to FIGS. 1 and 3.

A determination may be made (at block 470) whether a person is detected inside the enclosure of the disinfection tunnel. For example, the processor 195 may receive one or more signals from the motion detector 180 indicating that a person is still inside the disinfection tunnel. If it is determined (at block 470) that the motion detector detects a person inside the tunnel, the process 400 may return back to block 470, which was described above. Otherwise, one or more signals may be generated (at block 475) indicating that the disinfection tunnel is not occupied. For example, the processor 195 may turn on a light, display a message, and/or play an audio message indicating that the disinfection tunnel is not occupied. The process 400 may then end.

The specific operations of the process 400 may not be performed in the exact order shown and described. Furthermore, the specific operations described with reference to FIGS. 4A-4B may not be performed in one continuous series of operations in some embodiments, and different specific operations may be performed in different embodiments. For example, in some aspects of the present embodiments, the temperature of persons entering the disinfection tunnel may not be checked. In these embodiments, blocks 405-420 of the process 400 may be skipped. In some other aspects of the present embodiments, the temperature of persons entering the disinfection tunnel may be checked but the disinfection tunnel may not lock the entrance door if the persons' temperature is not normal. For example, the disinfection tunnel may not have an entrance door or the disinfection tunnel may have an entrance door but the door may not be lockable. In these embodiments, blocks 415 and/or 425 of the process 400 may be skipped.

In some embodiments, the ozonated water generator may have a sensor that checks the level of ozonated water in the ozonated water tank and may automatically fill in the ozonated water tank if the ozonated water level is less than a first threshold and may stop if the ozonated water level exceeds a second threshold. In these embodiments, blocks 445 and 465 of the process 400 may be skipped.

The use of ozonated water as the biocidal in the disinfection tunnel 100 provides the following technical advantages. The ozonated water is non-corrosive, non-irritant, non-sensitizer, and non-permeator to skin. The ozonated water is non-irritating to the eyes, non-hazardous in case of ingestion, non-hazardous in case of inhalation, non-irritant for lungs, and non-sensitizer for lungs. Although ozone in the gaseous state may be harmful, ozonated water poses no danger to humans and environment.

The stabilized ozonated water used as a disinfectant in the disinfection tunnel 100 provides the technical advantage that it does not leave any particular odors and instead eliminates the most stubborn odor molecules. The stabilized ozonated water complies with school and office building policies.

Furthermore, studies have shown that 99.99% of viruses are destroyed after a short, high-concentration ozone treatment. The ozonized water solution had been tested against an approved substitute for SARS-CoV-2, which is Coronavirus/MHV-3. MHV-3 (murine coronavirus/murine hepatitis virus) is one of the approved substitutes because it belongs to the same genus (betacoronavirus) as SARS (SARS-CoV), MERS (MERS-CoV) and COVID-19 (SARS-CoV-2). In tests against MHV-3, the laboratories have also tested against the influenza A (H1N1) virus, the measles virus and the respiratory syncytial virus. It has been established that after 30 seconds of exposure to this solution these microorganisms have been completely eradicated.

II. Large Flow Disinfection Tunnel

The disinfection tunnel described above is configured to disinfect a few persons, (e.g., one person, a person with one or more children, etc.) at every predetermined amount of time (e.g., and without limitations every 30 seconds). Take the example of a stadium, 80,000 people may need to be disinfected before they enter the stadium. If the stadium has 26 entrance gates (e.g., similar to "Stade de France" stadium), an average of almost 3,100 people has to pass by each gate. Using a disinfection tunnel configured to disinfect an individual person for 30 seconds may need more than 25 hours, which is not acceptable.

Figure 5:
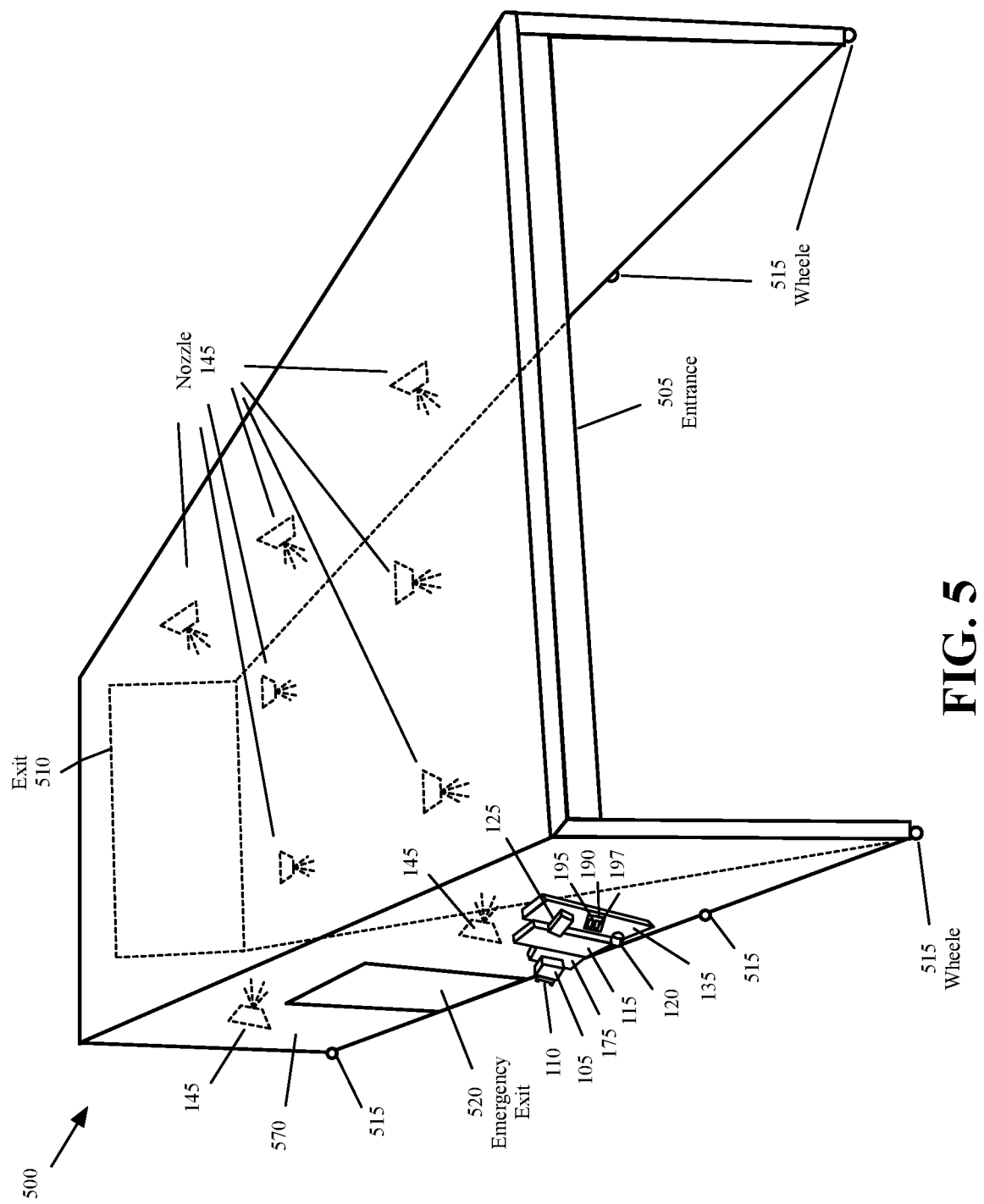
FIG. 5 is a front perspective of a large flow disinfection tunnel, according to various aspects of the present disclosure.

Some of the present embodiments provide a tunnel that is adapted for a large flow of people to pass through in a short time period, for example, and without limitations, in a place such as a mall, a stadium, an airport, etc. FIG. 5 is a front perspective of a large flow disinfection tunnel 500, according to various aspects of the present disclosure.

With reference to FIG. 5, the large flow disinfection tunnel 500 may be configured such that the tunnel 500 is long enough for people to advance for a predetermined amount of time (e.g., and without limitations, 30 seconds) inside the tunnel. For example, and without limitations, considering that people may walk at 1.4 meters/seconds, the large flow disinfection tunnel may be configured to be at least 21 meters long in some embodiments. Accordingly, the large flow disinfection tunnel 500, in some embodiments, may not include a timer to determine the amount of time to spray. Instead, the large flow disinfection tunnel 500 may include one or more motion detectors inside (not shown) that may detect the presence of people inside the tunnel and may continue activating the nozzles 145 as long as all people who have entered through the entrance 505 have not exited through the exit 510.

The large flow disinfection tunnel 500 may include components similar to the disinfection tunnel 100 of FIG. 1. For example, the large flow disinfection tunnel 500 may include an ozonated water generator 105, an ozonated water generator filter cartridge 110, an ozonated water tank 115, a water tank 175, a hydraulic pump 120, a mist generator 125, an electrical cabinet 135, a controller 190, a processor 195, computer readable media 197, one or more contactless gel dispensers, one or more ozonated water mist nozzles 145, a non-slip floor, and a waste storage, some of which are not shown for simplicity. In addition, the piping used for carrying the fluid between different components of the disinfection tunnel 500, such as, the water tank 175, the ozonated water generator 105, the ozonated water tank 115, the pump 120, the mist generator 125, the nozzles 145, etc., is not shown in FIG. 5 for simplicity.

Some embodiments may use a large ozonated water tank 115 that may store enough ozonated water for many hours spraying by the nozzles. The ozonated water generator 105 may be started ahead of an event and/or may operate during the tunnel's use in order to keep the level of ozonated water in the ozonated water tank 115 above a first threshold. The ozonated water generator 105 may keep on filling the ozonated water tank 115 until the level of ozonated water in the ozonated water tank 115 reaches a second, higher, threshold.

Some embodiments may include several ozonated water generators, ozonated water generators filter cartridges, ozonated water tanks, hydraulic pump, water tanks, and/or mist generators, depending on the size of the large flow disinfection tunnel 500. The capacity of the ozonated water generator(s), the capacity of the water tank(s), and/or the capacity of the ozonated water tank(s) may be varied depending on the size of the tunnel 500 and the number of nozzles 145 deployed. For example, for a tunnel that consumes 105 liters of disinfectant per hour (e.g., for a stadium, a mall, or an airport) one or more tanks with a total capacity of 600 liters or more may be used. Some embodiments may provide one or more emergency exits 520 on the tunnel's enclosure 570 at one or more locations in the middle of the tunnel to facilitate evacuation during an emergency and/or panic. Some embodiments may provide one or more windows (not shown) that may be opened or closed on the tunnel's enclosure 570 to provide aeration inside the tunnel and to make sure a humid atmosphere is not created by the ozonated water mist inside the large flow disinfection tunnel 500.

With further reference to FIG. 5, the large flow disinfection tunnel 500 provides the following technical advantages, in addition to the technical advantages of the tunnel 100 described above. The single large tunnel is easier to setup and dismantle (compared to many small tunnels). After finishing an event, the tunnel 500 may easily be put away. The tunnel 500 may be produced in large quantities. The tunnel 500 may be made fireproof (e.g., with classification M0 (non-combustible), M1 (combustible (non-flammable), M2 (combustible, flame retardant), etc.), and/or the tunnel may be UV and weather resistant. The large flow disinfection tunnel 500 is configured with easily replaceable material to lower the repair and replacement costs.

Figure 6:
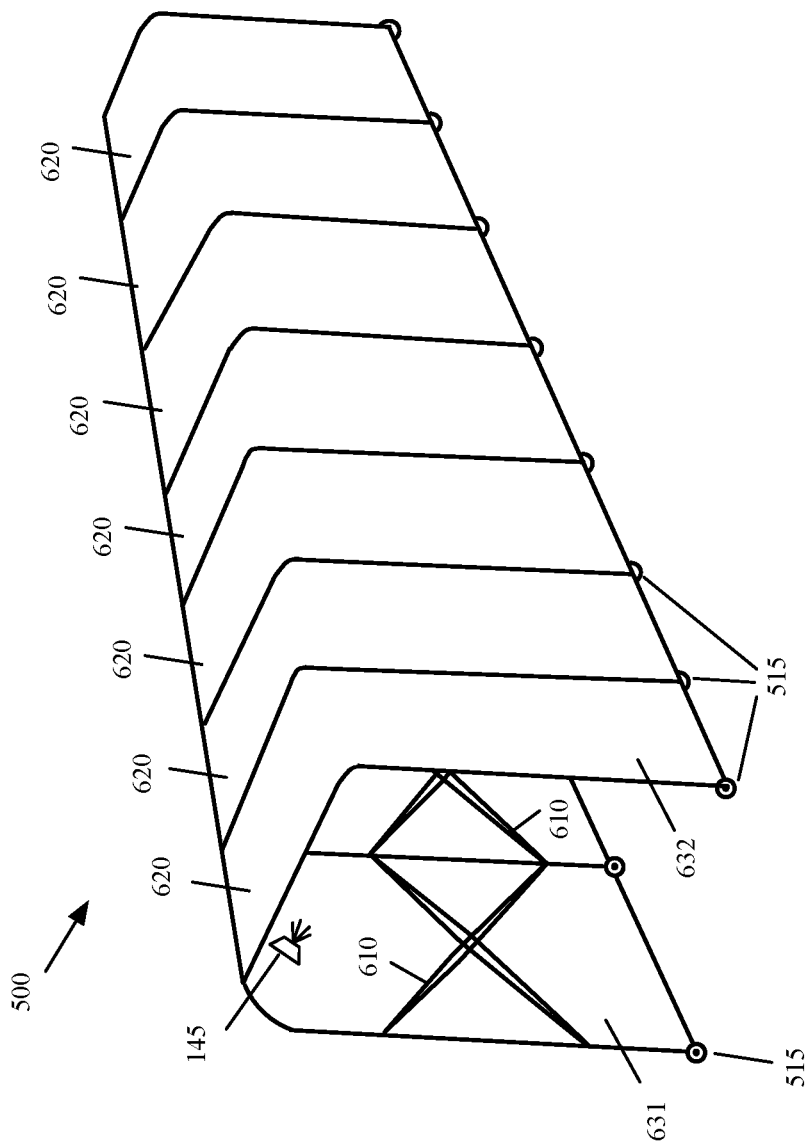
FIG. 6 is a front perspective of the large flow disinfection tunnel of FIG. 5 illustrating the retraction mechanism of the tunnel, according to various aspects of the present disclosure.

The large flow disinfection tunnel 500 may be retractable (or foldable), which provides the technical advantage of the ease of folding during deployment and ease of unfolding for storage. The large flow disinfection tunnel 500 may include several wheels 515 for ease of transportation and for adjusting the position of the tunnel. FIG. 6 is a front perspective of the large flow disinfection tunnel 500 of FIG. 5 illustrating the retraction mechanism of the tunnel, according to various aspects of the present disclosure.

With reference to FIG. 6, the large flow disinfection tunnel 500 may include components similar to the large flow disinfection tunnel 500 of FIG. 5, some of which are not shown for simplicity. As shown in FIG. 6, the large flow disinfection tunnel 500 may include several foldable sections 620. Each section may include a set of pantographs 610 that may be used to fold the section when the section is moved towards an adjacent section. Each section 620 may include at least one pantograph 610 on each opposite side 631 and 632 of the section (the pantograph(s) on the side 632 is/are not shown in the perspective view of FIG. 6). The wheels 515 facilitate the moving of each section towards an adjacent section during retracting. The wheels 515 facilitate the moving of each section away from an adjacent section during the tunnel's setup. The piping used for carrying the ozonated water from the ozonated water generator 105 to the nozzles 145 in some of the figures is not shown for simplicity.

The piping for the water and the ozonated water, in some of the disinfection tunnels of the present embodiments (e.g., the disinfection tunnel 100 of FIG. 1, the disinfection tunnel 500 of FIG. 5, and the disinfection tunnel 920 of FIG. 9), may use quick connect fitting (also referred to as push fittings). Quick connect fittings may be operated by hand and do not require wrenches. For example, some embodiments may use push-to-connect fittings (or instant fittings), which are a type of easily attached and removed compression fitting. The push-to-connect fittings may be used to quickly connect or remove the nozzles 145 to the pipes, without the use of wrenches, during the setup and retraction of the disinfection tunnels.

Figure 7:
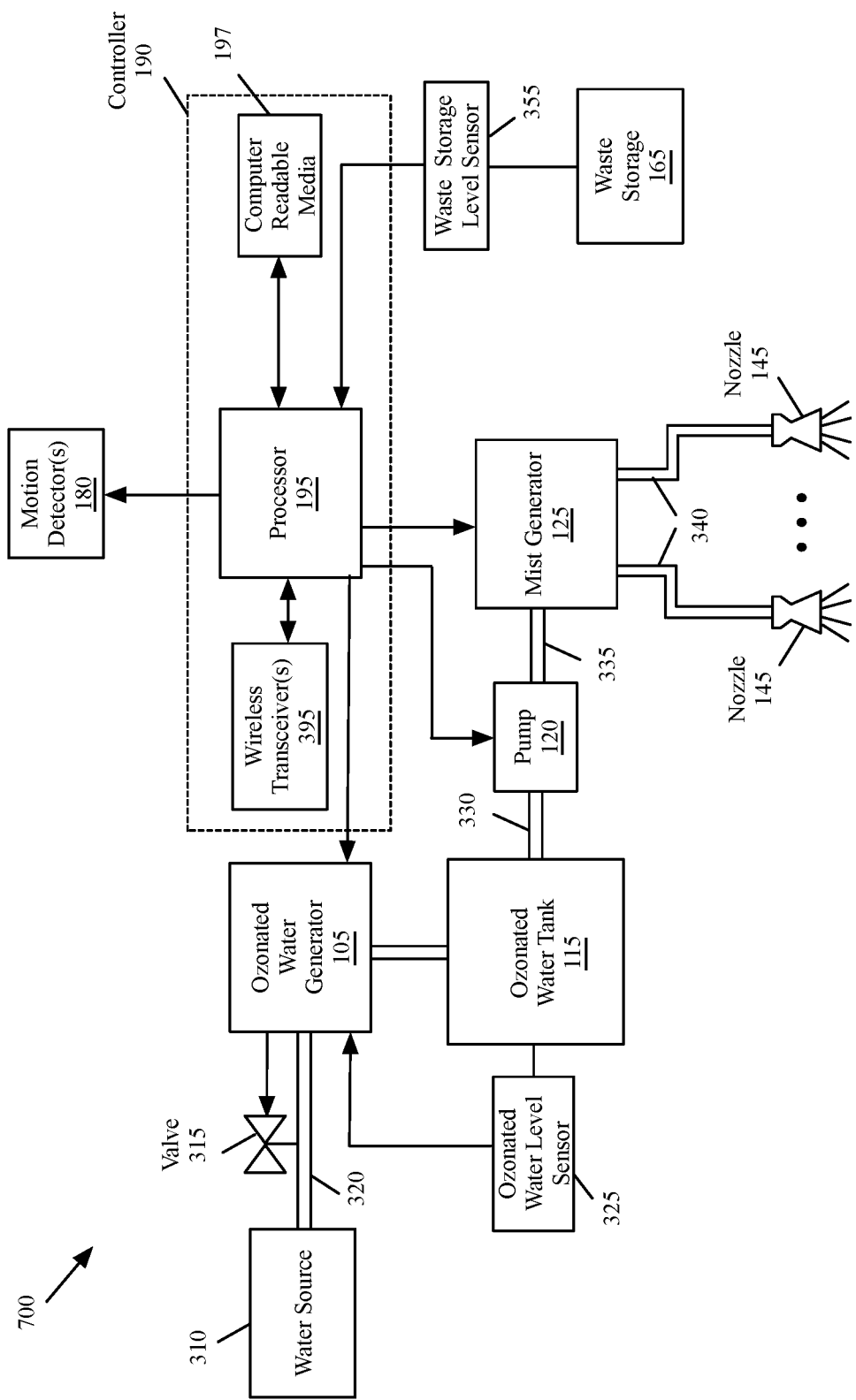
FIG. 7 is a functional block diagram illustrating an example mechanical and electrical system for the large flow disinfection tunnel of FIGS. 5 and 6, according to various aspects of the present disclosure.

FIG. 7 is a functional block diagram illustrating an example mechanical and electrical system for the large flow disinfection tunnel of FIGS. 5 and 6, according to various aspects of the present disclosure. With reference to FIG. 7, the system 700 may include a controller 190, a processor 195, computer readable media 197, one or more wireless transceivers 395, an ozonated water generator 105, an ozonated water tank 115, a pump 120, a mist generator 125, one or more motion detectors 180, a water source 310, an ozonated water level sensor 325, one or more wireless transceivers 395, a waste storage 165, and/or a waste storage level sensor 355, which may be similar to the corresponding components of the system 300, described above. It should be noted that some of the components of FIG. 7, such as, the ozonated water level sensor 325, the wireless transceiver(s) 395, the waste storage 165, and/or the waste storage level sensor 355 may be optional and some of the present embodiments may not include one or more of these components.

Since the large flow disinfection tunnel is for simultaneous use by multiple persons, the system 700 may not include the mist timer 130, the entrance light(s) 150, the temperature sensor 155, the alert signal generator 345, and/or the door controller 350 of the system 300. For example, as described above with reference to FIG. 5, the large flow disinfection tunnel may include one or more motion detectors inside the tunnel that may detect the presence of people inside the tunnel and the processor 195 may keep the mist generator 125 activated as long as all persons have not exited the tunnel. The motion detector(s) may send one or more signals to the processor 195 indicating that at least one person is moving inside the enclosure of the disinfection tunnel 500. When the motion detector(s) do not generate any signals for a predetermined time period, the processor 195 may stop the mist generator 125.

As another example, some embodiments may include a temperature detection station (not shown) at a distance (e.g., few meters) before the entrance of the large flow disinfection tunnel. The temperature detection station may include one or more temperature detection thermal cameras. The temperature detection station may include a controller that analyses the videos takes by the cameras, detects approaching persons' faces, and determines the body temperature of the persons. If the body temperature of a person is above a threshold indicating that the person may have a fever, the face of the person may be identified on a display (e.g., and without limitation, with a red circle) and personnel working at the temperature detection station may be alerted to prevent that person with high body temperature to move towards, and enter, the disinfection tunnel.

Figure 8:
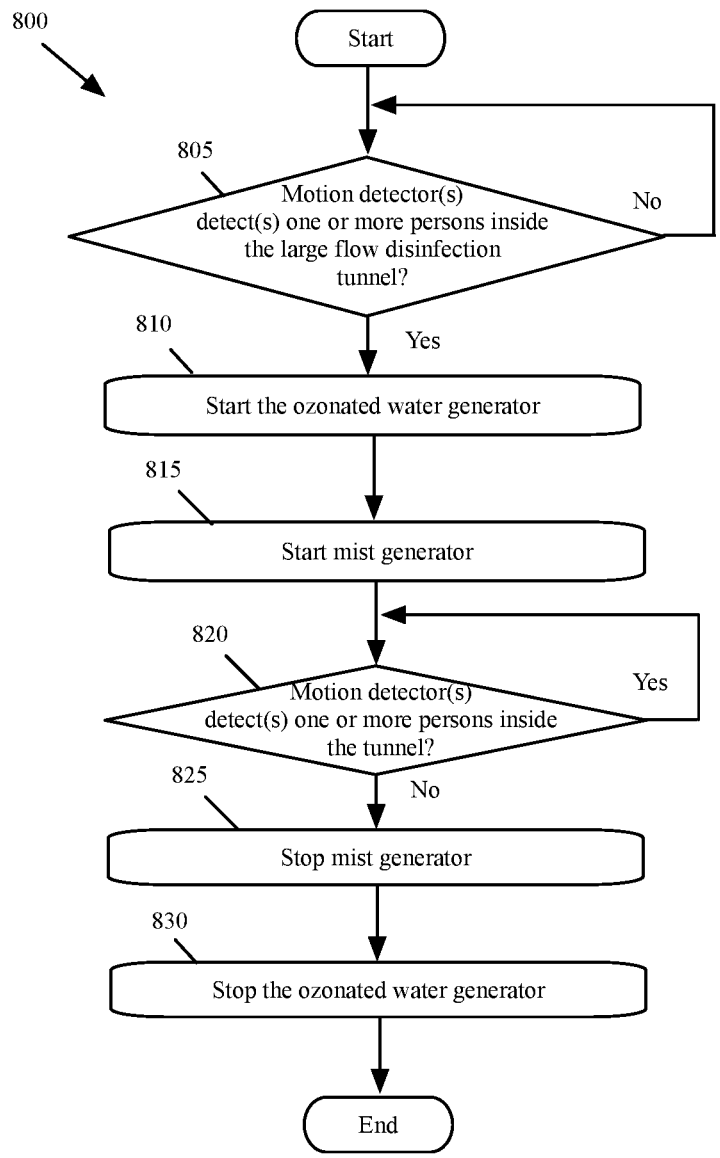
FIG. 8 is a flowchart illustrating an example process for controlling a large flow disinfection tunnel, according to various aspects of the present disclosure.

FIG. 8 is a flowchart illustrating an example process 800 for controlling a large flow disinfection tunnel, according to various aspects of the present disclosure. The process 800, in some embodiments, may be performed by the processor 195 (FIGS. 5 and 7) of a large flow disinfection tunnel.

With reference to FIG. 8, a determination may be made (at block 805) whether the motion detector(s) detect(s) one or more persons inside the disinfection tunnel. For example, the processor 195 (FIGS. 5 and 7) may receive one or more signals from the motion detector(s) 180 indicating that one or more persons have entered the disinfection tunnel. When a determination is made (at block 805) that the motion detector(s) has/have not detected any persons inside the disinfection tunnel, the process 800 may proceed to block 805, which was described above.

Otherwise, the ozonated water generator may be started (at block 810). For example, the processor 195 of FIGS. 5 and 7 may start the ozonated water generator 105. At block 815, the mist generator may be started. For example, the processor 195 of FIGS. 5 and 7 may start the mist generator 125.

A determination may be made (at block 820) whether the motion detector(s) detect(s) one or more persons inside the disinfection tunnel. If one or more persons are detected inside the large flow disinfection tunnel, the process 800 may proceed back to block 820, which was described above. Otherwise, when the motion detector(s) do not detect any persons moving inside the disinfection tunnel's enclosure for a predetermined time period, the mist generator may be stopped (at block 825). For example, the processor 195 of FIGS. 5 and 7 may generate one or more signals to stop the mist generator 125. At block 830, the ozonated water generator may be stopped. For example, the processor 195 of FIGS. 5 and 7 may generate one or more signals to stop the ozonated water generator 105. The process 800 may then exit.

The specific operations of the process 800 may not be performed in the exact order shown and described. Furthermore, the specific operations described with reference to FIG. 8 may not be performed in one continuous series of operations in some embodiments, and different specific operations may be performed in different embodiments. For example, in some aspects of the present embodiments, the ozonated water generator may have a sensor that checks the level of ozonated water in the ozonated water tank and may automatically fill in the ozonated water tank if the ozonated water level is less than a first threshold and may stop if the ozonated water level exceeds a second threshold. In these embodiments, blocks 810 and 830 of the process 800 may be skipped.

III. Disinfection Tunnel for Inanimate Objects

Figure 9:
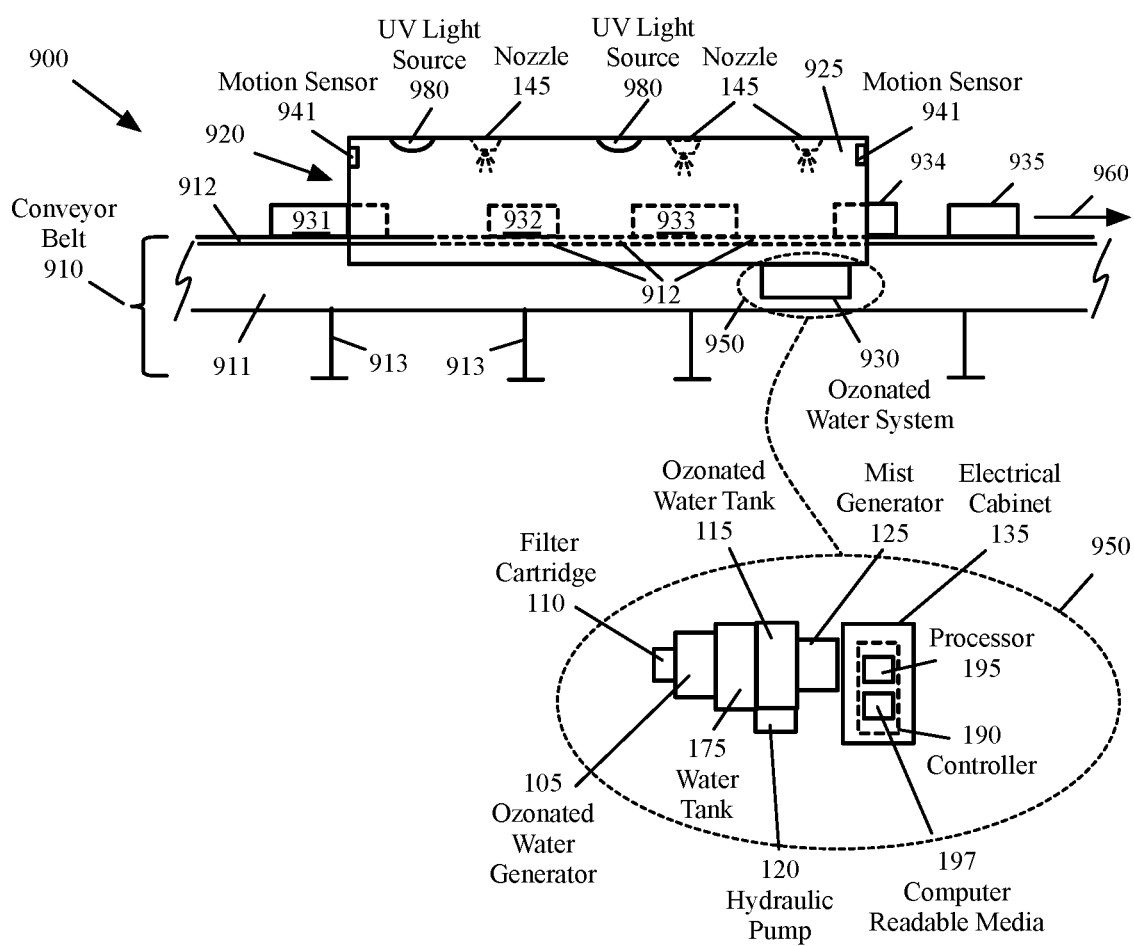
FIG. 9 is a side elevation view of a system for disinfecting inanimate objects that move over a conveyor belt, according to various aspects of the present disclosure.
Figure 10:
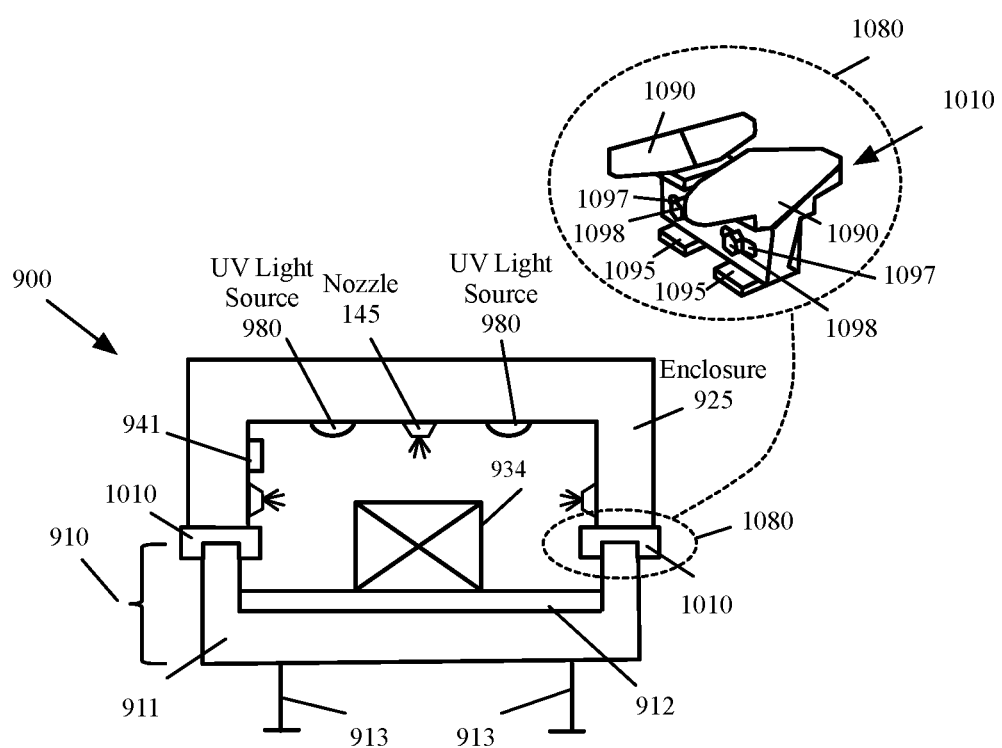
FIG. 10 is a front elevation view of the system of FIG. 9, according to various aspects of the present disclosure.

Some embodiments provide a disinfection tunnel for inanimate objects. FIG. 9 is a side elevation view of a system for disinfecting inanimate objects that move over a conveyor belt, according to various aspects of the present disclosure. FIG. 10 is a front elevation view of the system of FIG. 9, according to various aspects of the present disclosure. With reference to FIGS. 9 and 10, the system 900 may include a conveyor belt 910 and a disinfection tunnel 920.

The conveyor belt 910 may be used to move inanimate objects 931-935 such as baggage, packages, parcels, etc. Example of such a conveyor belt 910 include baggage carousels in the airports, package and parcel conveyor belts in shipping companies and post offices, etc. The conveyor belt 910 may include a stationary body portion 911 and a moving portion 912. The stationary body portion 911 may be optionally positioned on the poles 913 or stationary body portion 911 may be placed on the floor.

The moving portion 912 may be a relatively thin surface, such as metal, rubber, plastic, etc., that may include separate sections that move over a group of rollers (not shown). The objects 931-935 may be placed on the moving portion 912 at a loading area. The objects may be moved, for example, in the direction of the arrow 960, by the moving portion 912 to a delivery area. The moving portion 912 may continue back to the loading area.

It should be noted that the conveyor belt 910 may form a closed loop to facilitates moving objects, for example, from the loading area to the delivery area. The disinfection tunnel 920 may also have a curved contour to match the shape of a portion of conveyor belt 910. For simplicity, the elevation view of FIG. 10 does not show any curved portions of the conveyor belt 910 and/or any curved portions of the disinfection tunnel 920.

The enclosure 925 of the disinfection tunnel 920 may be made of material such as, for example, and without limitations, metal, plastic, etc., and may be configured to fit over a portion of the conveyor belt 910. For example, the disinfection tunnel 920 may include several adaptable grippers 1010 (FIG. 10) along each side of the tunnel. The grippers 1010 may be configured to attach to the edges of the conveyor belt such that the disinfection tunnel 920 may seal around the conveyor belt 920. The grippers 1010 may enable holding, tightening, handling, and release of the edges of the conveyor belt 920.

As shown by the expanded view 1080, the gripper 1010 may include two gripping pads 1095. Each of the gripping pads 1095 may be connected to a bolt 1098 that may move along a slot 1097. The distance between the gripping pads 1095 may be adjusted by loosening the bolts 1090 and moving the gripping pads 1095 towards or away each other. Once the distance between the gripping pads 1095 is adjusted to fit the edge of a particular conveyor belt, the bolts 1090 may be tightened.

Figure 12:
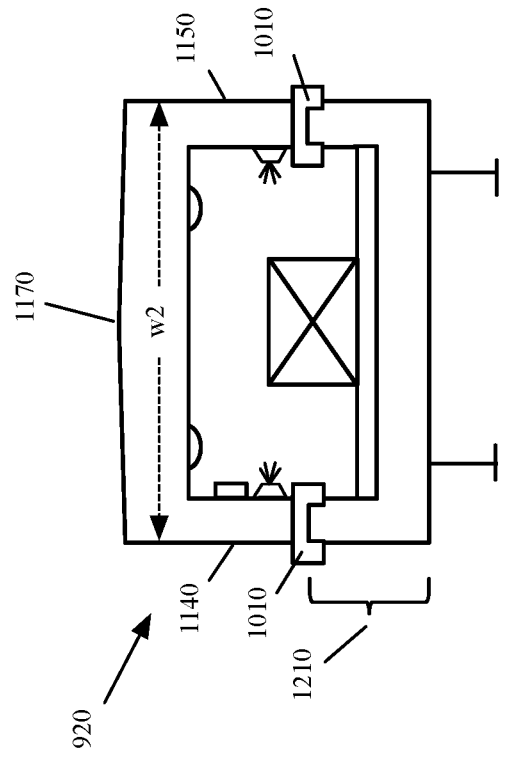
FIGS. 11 and 12 are examples of a disinfection tunnel that is adjustable to fit on conveyor belts with different widths, according to various aspects of the present disclosure.
Figure 11:
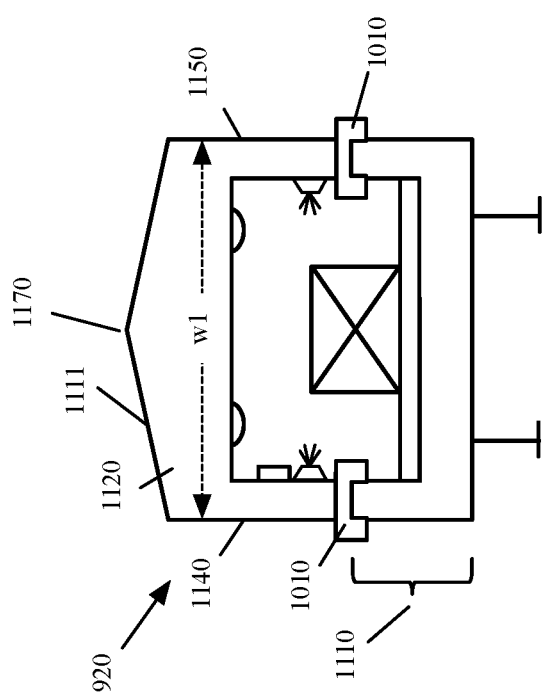

The disinfection tunnel, in some embodiments, may be configured to adjust to the width of different conveyor belts. FIGS. 11 and 12 are examples of a disinfection tunnel that is adjustable to fit on conveyor belts with different widths, according to various aspects of the present disclosure. With reference to FIG. 11, the disinfection system 1100 may include an adjustable disinfection tunnel 920. The top portion of the disinfection tunnel 920 may be foldable across a top rib 1170, which is shown as a point in the front view of FIG. 11.

The two sides 1140 and 1150 of the tunnel 1120 may be pushed towards each other, causing the rib 1170 to move up and reduce the width of the tunnel 1120. The two sides 1140 and 1150 of the tunnel 920 may be pulled away from each other to cause the rib 1170 to move down and increase the width of the tunnel 920.

As shown in the examples of FIGS. 11 and 12, the width of the conveyor belt 1210 is more than the width of the conveyor belt 1110. The disinfection tunnel 920 has been adjusted such the width, w2, of the tunnel 920 of FIG. 12 is more than the width, w1, of the tunnel 920 of FIG. 11. The tunnel 900 may, therefore, be adjusted on the field to match the widths of different conveyor belts.

Figure 13:
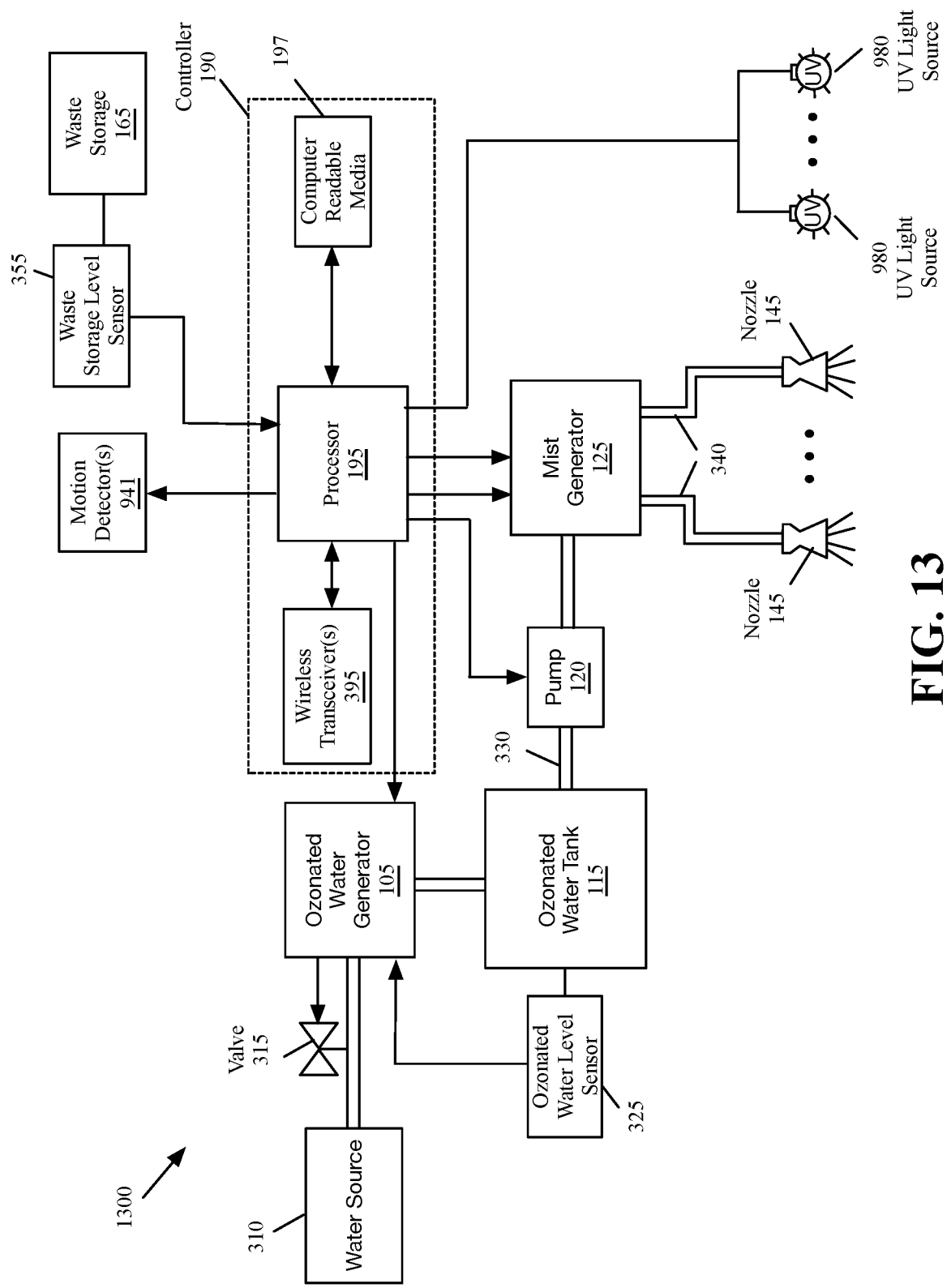
FIG. 13 is a functional block diagram illustrating an example mechanical and electrical system for the disinfection tunnel of FIGS. 9-12, according to various aspects of the present disclosure.

The disinfection tunnel 920 may include an ozonated water system 930 (FIG. 9). As shown in the expanded view 950, the ozonated water system 930 may include an ozonated water generator 105, an ozonated water generator filter cartridge 110, an ozonated water tank 115, a water tank 175, a hydraulic pump 120, a mist generator 125, an electrical cabinet 135, a controller 190, a processor 195, and/or computer readable media 197. The ozonated water system 930 may also include one or more ozonated water mist nozzles 145, a waste storage (not shown). The components of the ozonated water system 930 may function as the corresponding components of FIG. 1. FIG. 13, described below, illustrates further details of the ozonated water system 930. The piping used for carrying the fluid between different components of the disinfection tunnel 920 is not shown for simplicity.

The disinfection tunnel 920, in some embodiments, may include one or more UV light sources 980. The UV light have sterilization and disinfection effects by destroying the molecular structure of microorganisms, such as viruses, bacteria, and fungi. The UV rays are divided into A, B, C, and D bands, and the microorganisms disinfection effect is most effective in the C band (UVC) with a wavelength of 200-280 nm (nanometer). In the embodiments that include UV light sources, the disinfection tunnel may be configured to prevent the UV light to leak out of the enclosure 925 of the disinfection tunnel 920. The enclosure 925 may be configured to tightly fit over the conveyor belt, the enclosure material (e.g., and without limitations, may be selected from metal, opaque plastic, etc.) to prevent the leaking of the UV light to the outside of the enclosure. Some of these embodiments may include pads (not shown) that may be hanged at the entrance and the exit of the tunnel 920. The pads may be, for example, and without limitations, connected to the upper side of the entrance and exit of the tunnel 920. The pads may be opaque to UV light. The objects 931-935 may push against the loose bottom of the pads to enter and exit the tunnel 920.

With further reference to FIG. 9, the disinfection tunnel 920 may include one or more motion detectors 941 to detect whether any object 931-935 is moving inside the disinfection tunnel 920 and/or whether all objects 931-935 have exited the disinfection tunnel 920.

The disinfection tunnel 920 may be configured such that the enclosure 925 is long enough for the objects that are placed over the conveyor belt 912 to remain inside the tunnel for a predetermined amount of time. For example, and without limitations, the speed of the conveyor belt movement may be determined and the enclosure of the disinfection tunnel may be configured to be long enough such that the objects that are placed over the conveyor belt and enter the tunnel would remain inside the tunnel for a predetermined amount of time before exiting the tunnel to get disinfected.

When the motion detector(s) 941 detect(s) that any object 931-935 is/are still inside the tunnel (e.g., by detecting whether an object 931-935 placed over the conveyor belt 910 is moving inside the tunnel), the processor 195 of the tunnel 920 may trigger a misting operation by the mist generator 125. The misting operation may continue as long as any object is moving over the conveyor belt inside the tunnel 900. In the embodiments that include UV lights inside the tunnel 900, the processor 195 of the tunnel 900 may turn the UV lights on as long as any object is moving inside the tunnel.

FIG. 13 is a functional block diagram illustrating an example mechanical and electrical system for the disinfection tunnel of FIGS. 9-12, according to various aspects of the present disclosure. With reference to FIG. 13, the system 1300 may include a controller 190, a processor 195, computer readable media 197, one or more wireless transceivers 395, an ozonated water generator 105, an ozonated water tank 115, a pump 120, a mist generator 125, one or more motion detectors 941, a water source 310, an ozonated water level sensor 325, one or more wireless transceivers 395, a waste storage 165, and/or a waste storage level sensor 355, which may be similar to the corresponding components of the system 300, described above. The system 1300 may include one or more UV light sources 980 that may be activated by the processor 195 when the motion detector(s) detect any objects moving over the conveyor belt inside the disinfection tunnel.

Since the disinfection tunnel is configured for disinfecting groups of inanimate objects moving close to each other, the system 1300 may not include the mist timer 130, the entrance light(s) 150, the temperature sensor 155, the alert signal generator 345, and/or the door controller 350 of the system 300. For example, as described above with reference to FIG. 9, the disinfection tunnel 900 may include one or more motion detectors 941 inside the tunnel that may detect the presence of moving objects placed over the conveyor belt inside the tunnel and the processor 195 may continue activating the nozzles 145 as long as any of the objects is moving inside the tunnel.

Some embodiments may use a large ozonated water tank 115 that may store enough ozonated water for many hours spraying by the nozzles. The ozonated water generator 105 may be started ahead of using the conveyor belt to move objects and/or may operate during the tunnel's use in order to keep the level of ozonated water in the ozonated water tank 115 above a first threshold. The ozonated water generator 105 may keep on filling the ozonated water tank 115 until the level of ozonated water in the ozonated water tank 115 reaches a second, higher, threshold.

It should be noted that some of the components of FIG. 13, such as, the ozonated water level sensor 325, the wireless transceiver(s) 395, the waste storage 165, and/or the waste storage level sensor 355 may be optional and some of the present embodiments may not include one or more of these components. Since the tunnel 920 may be installed over a conveyor belt at a permanent location, some embodiments may connect the waste storage 165 to a municipal sewage system to eliminate the need for manually emptying the waste storage 165. In these embodiments, the waste storage level sensor 355 may be used to ensure the piping to the sewage system is not clogged. The processor 195 may generate one or more alert signals if the level of liquid in the waste storage 165 exceeds a threshold.

Figure 14:
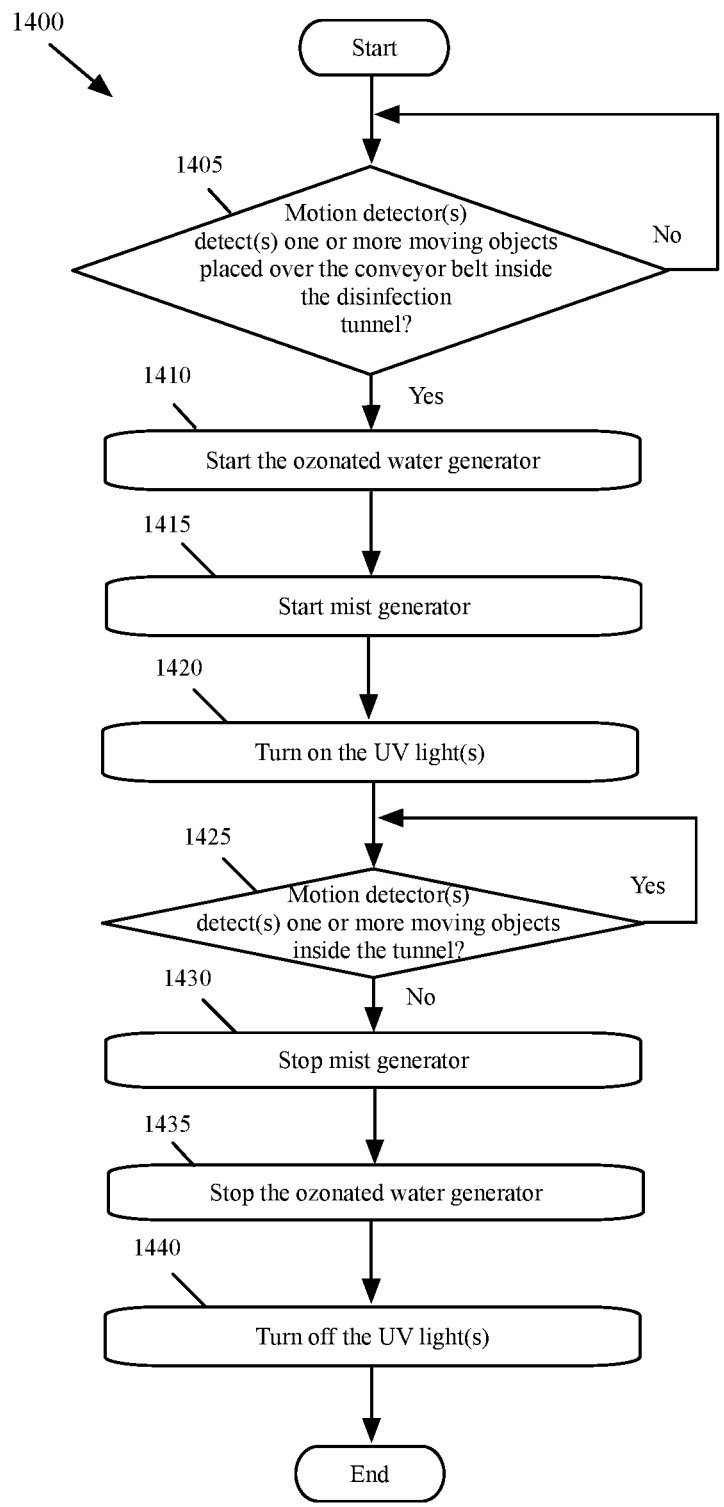
FIG. 14 is a flowchart illustrating an example process for controlling a disinfection tunnel for disinfecting inanimate objects, according to various aspects of the present disclosure.

FIG. 14 is a flowchart illustrating an example process 1400 for controlling a disinfection tunnel for disinfecting inanimate objects, according to various aspects of the present disclosure. The process 1400, in some embodiments, may be performed by the processor 195 (FIGS. 9 and 13) of the disinfection tunnel 920.

With reference to FIG. 14, a determination may be made (at block 1405) whether the motion detector(s) detect(s) one or more moving objects placed over the conveyor belt inside the disinfection tunnel. For example, the processor 195 (FIGS. 9 and 13) may receive one or more signals from the motion detector(s) 180 indicating that one or more objects placed over the conveyor belt are moving inside the disinfection tunnel. When a determination is made (at block 1405) that the motion detector(s) has/have not detected any moving objects inside the disinfection tunnel, the process 1400 may proceed to block 1405, which was described above.

Otherwise, the ozonated water generator may be started (at block 1410). For example, the processor 195 of FIGS. 9 and 13 may start the ozonated water generator 105. At block 1415, the mist generator may be started. For example, the processor 195 of FIGS. 9 and 13 may start the mist generator 125. The UV lights sources may be turned on (at block 1420). For example, the processor 195 of FIGS. 9 and 13 may turn on the UV lights sources 980.

A determination may be made (at block 1425) whether the motion detector(s) detect(s) one or more moving objects placed over the conveyor belt inside the disinfection tunnel. When one or more moving objects are detected inside the large flow disinfection tunnel, the process 1400 may proceed back to block 1425, which was described above. Otherwise, the mist generator may be stopped (at block 1430). For example, the processor 195 of FIGS. 9 and 13 may generate one or more signals to stop the mist generator 125. At block 1435, the ozonated water generator may be stopped. For example, the processor 195 of FIGS. 9 and 13 may generate one or more signals to stop the ozonated water generator 105. At block 1440, the UV lights may be turned off. For example, the processor 195 of FIGS. 9 and 13 may generate one or more signals to turn off the UV light sources 980. The process 1400 may then exit.

The specific operations of the process 1400 may not be performed in the exact order shown and described. Furthermore, the specific operations described with reference to FIG. 14 may not be performed in one continuous series of operations in some embodiments, and different specific operations may be performed in different embodiments. For example, in some aspects of the present embodiments, the ozonated water generator may have a sensor that checks the level of ozonated water in the ozonated water tank and may automatically fill in the ozonated water tank if the ozonated water level is less than a threshold. In these embodiments, blocks 1410 and 1435 of the process 1400 may be skipped. Some embodiments may not include the UV lights. In these embodiments, blocks 1420 and 1440 may be skipped.

In a first aspect, a disinfection tunnel, comprises: an enclosure; an ozonated water tank; an ozonated water generator configured to: receive water; receive oxygen, generate ozone from the oxygen; infuse the water with the ozone to generate ozonated water; and store the ozonated water in the ozonated water tank; a set of one or more nozzles located inside the enclosure, the set of nozzles configured to: receive a mist of ozonated water; and spray the mist of ozonated water; a mist generator connected to the set of nozzles through a set of one or more pipes, the mist generator configured to: receive the ozonated water; generate a mist of ozonated water; and transfer the mist of ozonated water to the set of nozzles through the set of pipes; a pump configured to transfer the ozonated water from the ozonated water tank to the mist generator; a processor configured to: receive one or more signals indicating that a person is inside the enclosure; in response to receiving the one or more signals: start the pump; start the mist generator; after a predetermined time period: stop the mist generator; and stop the pump.

In a second aspect, a large flow disinfection tunnel, comprises: an enclosure configured to encompass a plurality of persons; an ozonated water tank; an ozonated water generator configured to: receive water; receive oxygen, generate ozone from the oxygen; infuse the water with the ozone to generate ozonated water; and store the ozonated water in the ozonated water tank; a set of one or more nozzles located inside the enclosure, the set of nozzles configured to: receive a mist of ozonated water; and spray the mist of ozonated water; a mist generator connected to the set of nozzles through a set of one or more pipes, the mist generator configured to: receive the ozonated water; generate a mist of ozonated water; and transfer the mist of ozonated water to the set of nozzles through the set of pipes; a set of one or more motion detectors configured to: detect that at least one person is moving inside the enclosure; and generate one or more signals in response to the detection; a pump configured to transfer the ozonated water from the ozonated water tank to the mist generator; a processor configured to: receive the one or more signals from the set of motion detectors; start the pump; start the mist generator; when no signal is received from the set of motion detectors for a predetermined time period: stop the mist generator; and stop the pump.

In a third aspect, a disinfection tunnel for disinfecting inanimate objects comprises: an enclosure configured to fit over a portion of a conveyor belt, the conveyor belt configured to move inanimate objects between first and second locations; an ozonated water tank; an ozonated water generator configured to: receive water; receive oxygen, generate ozone from the oxygen; infuse the water with ozone to generate ozonated water; and store the ozonated water in the ozonated water tank; a set of one or more nozzles located inside the enclosure, the set of nozzles configured to: receive a mist of ozonated water; and spray the mist of ozonated water; a mist generator connected to the set of nozzles through a set of one or more pipes, the mist generator configured to: receive ozonated water; generate a mist of ozonated water; and transfer the mist of ozonated water to the set of nozzles through the set of pipes; a set of one or more motion detectors configured to: detect that at least one object placed over the conveyor belt is moving inside the enclosure; and generate one or more signals in response to the detection; a pump configured to transfer ozonated water from the ozonated water tank to the mist generator; a processor configured to: receive the one or more signals from the set of motion detectors indicating that at least one object placed over the conveyor belt is moving inside the enclosure; start the pump; start the mist generator; when no signal is received from the set of motion detectors for a predetermined time period indicating that at least one object placed over the conveyor belt is moving inside the enclosure: stop the mist generator; and stop the pump.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure.

What is claimed is:

1. A disinfection tunnel, comprising:
   an enclosure;
   an ozonated water tank;
   an ozonated water generator configured to:
      receive water;
      receive oxygen,
      generate ozone from the oxygen;
      infuse the water with the ozone to generate ozonated water; and
      store the ozonated water in the ozonated water tank;
   a set of one or more nozzles located inside the enclosure, the set of nozzles configured to:
      receive a mist of ozonated water; and
      spray the mist of ozonated water;
   a mist generator connected to the set of nozzles through a set of one or more pipes, the mist generator configured to:
      receive the ozonated water;
      generate a mist of ozonated water; and
      transfer the mist of ozonated water to the set of nozzles through the set of pipes;
   a pump configured to transfer the ozonated water from the ozonated water tank to the mist generator;
   a processor configured to:
      receive one or more signals indicating that a person is inside the enclosure;
      in response to receiving the one or more signals:
         start the pump;
         start the mist generator;
      after a predetermined time period:
         stop the mist generator; and
         stop the pump.

2. The disinfection tunnel of claim 1 further comprising:
   a motion detector configured to:
      detect that a person has entered the enclosure; and
      in response to detecting that the person is inside the enclosure, generate said one or more signals indicating that a person is inside the enclosure; and
      send the one or more signals to the processor.

3. The disinfection tunnel of claim 1, wherein the ozonated water generator is configured to receive the water from one of a tap water pipe and a water tank.

4. The disinfection tunnel of claim 1, wherein the ozonated water generator is configured to receive the oxygen from the surrounding air through an air intake.

5. The disinfection tunnel of claim 1 further comprising:
a temperature sensor configured to:
measure a body temperature of persons approaching the disinfection tunnel; and
send the temperature measurements to the processor,
wherein the processor is configured to:
compare the temperature measurements with a threshold; and
generate an alert indicating that the person has high temperature when a temperature measurement received from the temperature sensor is above the threshold.

6. The disinfection tunnel of claim 5, wherein the alert is at least one of turning a light, displaying a message, and playing an audible sound.

7. The disinfection tunnel of claim 5 further comprising an entrance door to the enclosure, wherein the processor is configured to:
compare the temperature measurements with a threshold;
lock the entrance door when a temperature measurement received from the temperature sensor is above the threshold.

8. The disinfection tunnel of claim 1 further comprising:
an ozonated water level sensor inside the ozonated water tank, the ozonated water level sensor configured to:
measure a level of the ozonated water in the ozonated water tank; and
send the measurement to the processor,
wherein the processor is configured to:
compare the ozonated water level measurement received from the ozonated water level sensor with first and second thresholds, wherein the second threshold is higher than the first threshold;
start the ozonated water generator to store ozonated water in the ozonated water tank when the ozonated water level measurement is below the first threshold; and
stop the ozonated water generator when the ozonated water level measurement exceeds the second threshold.

9. The disinfection tunnel of claim 1, wherein the processor is configured to:
start a timer configured to identify a duration of the spray by the nozzles in response to receiving the one or more signals from the motion detector; and
stop the pump and stop the mist generator in response to determining that the timer has expired.

10. A large flow disinfection tunnel, comprising:
an enclosure configured to encompass a plurality of persons;
an ozonated water tank;
an ozonated water generator configured to:
receive water;
receive oxygen,
generate ozone from the oxygen;
infuse the water with the ozone to generate ozonated water; and
store the ozonated water in the ozonated water tank;
a set of one or more nozzles located inside the enclosure, the set of nozzles configured to:
receive a mist of ozonated water; and
spray the mist of ozonated water;
a mist generator connected to the set of nozzles through a set of one or more pipes, the mist generator configured to:
receive the ozonated water;
generate a mist of ozonated water; and
transfer the mist of ozonated water to the set of nozzles through the set of pipes;
a set of one or more motion detectors configured to:
detect that at least one person is moving inside the enclosure; and
generate one or more signals in response to the detection;
a pump configured to transfer the ozonated water from the ozonated water tank to the mist generator;
a processor configured to:
receive the one or more signals from the set of motion detectors;
start the pump;
start the mist generator;
when no signal is received from the set of motion detectors for a predetermined time period:
stop the mist generator; and
stop the pump.

11. The large flow disinfection tunnel of claim 10, wherein the ozonated water generator is configured to receive the water from one of a tap water pipe and a water tank.

12. The large flow disinfection tunnel of claim 10, wherein the ozonated water generator is configured to receive the oxygen from the surrounding air through an air intake.

13. The large flow disinfection tunnel of claim 10 further comprising:
an ozonated water level sensor inside the ozonated water tank, the ozonated water level sensor configured to:
measure a level of the ozonated water in the ozonated water tank; and
send the measurement to the processor,
wherein the processor is configured to:
compare the ozonated water level measurement received from the ozonated water level sensor with first and second thresholds, wherein the second threshold is higher than the first threshold;
start the ozonated water generator to store ozonated water in the ozonated water tank when the ozonated water level measurement is below the first threshold; and
stop the ozonated water generator when the ozonated water level measurement exceeds the second threshold.

14. The large flow disinfection tunnel of claim 10,
wherein the enclosure comprises a plurality of foldable sections, and
wherein the disinfection tunnel comprises a plurality of wheels under each foldable section, wherein the wheels are configured to facilitate moving each section towards or away from an adjacent section.

15. The large flow disinfection tunnel of claim 14, wherein each foldable section comprises a plurality of pantographs configured to fold and unfold the foldable section.

16. A disinfection tunnel for disinfecting inanimate objects, the disinfection tunnel comprising:
an enclosure configured to fit over a portion of a conveyor belt, the conveyor belt configured to move inanimate objects between first and second locations;
an ozonated water tank;

an ozonated water generator configured to:
  receive water;
  receive oxygen,
  generate ozone from the oxygen;
  infuse the water with ozone to generate ozonated water; and
  store the ozonated water in the ozonated water tank;
a set of one or more nozzles located inside the enclosure, the set of nozzles configured to:
  receive a mist of ozonated water; and
  spray the mist of ozonated water;
a mist generator connected to the set of nozzles through a set of one or more pipes, the mist generator configured to:
  receive ozonated water;
  generate a mist of ozonated water; and
  transfer the mist of ozonated water to the set of nozzles through the set of pipes;
a set of one or more motion detectors configured to:
  detect that at least one object placed over the conveyor belt is moving inside the enclosure; and
  generate one or more signals in response to the detection;
a pump configured to transfer ozonated water from the ozonated water tank to the mist generator;
a processor configured to:
  receive the one or more signals from the set of motion detectors indicating that at least one object placed over the conveyor belt is moving inside the enclosure;
  start the pump;
  start the mist generator;
  when no signal is received from the set of motion detectors for a predetermined time period indicating that at least one object placed over the conveyor belt is moving inside the enclosure:
    stop the mist generator; and
    stop the pump.

17. The disinfection tunnel of claim 16 further comprising a plurality of adjustable connectors configured to connect the enclosure to an edge of the conveyor belt.

18. The disinfection tunnel of claim 16, wherein the ozonated water generator is configured to receive the water from one of a tap water pipe and a water tank.

19. The disinfection tunnel of claim 16, wherein the ozonated water generator is configured to receive the oxygen from the surrounding air through an air intake.

20. The disinfection tunnel of claim 16 further comprising:
an ozonated water level sensor inside the ozonated water tank, the ozonated water level sensor configured to:
  measure a level of the ozonated water in the ozonated water tank; and
  send the measurement to the processor,
wherein the processor is configured to:
  compare the ozonated water level measurement received from the ozonated water level sensor with first and second thresholds, wherein the second threshold is higher than the first threshold;
  when the ozonated water level measurement is below the first threshold, start the ozonated water generator to store ozonated water in the ozonated water tank; and
  when the ozonated water level measurement exceeds the second threshold, stop the ozonated water generator.

21. The disinfection tunnel of claim 16 further comprising:
a set of one or more ultraviolet (UV) light sources located inside the enclosure, the UV light sources configured to generate UV light,
wherein the processor is configured to:
  turn on the set of UV light sources on after receiving the one or more signals from the set of motion detectors indicating that at least one object placed over the conveyor belt is moving inside the enclosure; and
  turn off the UV light sources when no signal is received from the set of motion detectors for the predetermined time period.

* * * * *